US012766324B2

(12) United States Patent
Dayeh et al.

(10) Patent No.: US 12,766,324 B2
(45) Date of Patent: Oct. 20, 2026

(54) MULTI-HUNDRED OR THOUSAND CHANNEL ELECTRODE ELECTROPHYSIOLOGICAL ARRAY AND FABRICATION METHOD

(71) Applicant: THE REGENTS OF THE UNIVERSITY OF CALIFORNIA, Oakland, CA (US)

(72) Inventors: Shadi A. Dayeh, San Diego, CA (US); Youngbin Tchoe, San Diego, CA (US); Andrew M. Bourhis, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 249 days.

(21) Appl. No.: 18/547,999

(22) PCT Filed: Mar. 10, 2022

(86) PCT No.: PCT/US2022/019778
§ 371 (c)(1),
(2) Date: Aug. 25, 2023

(87) PCT Pub. No.: WO2022/192560
PCT Pub. Date: Sep. 15, 2022

(65) Prior Publication Data

US 2024/0131339 A1 Apr. 25, 2024
US 2024/0226565 A9 Jul. 11, 2024

Related U.S. Application Data

(60) Provisional application No. 63/160,107, filed on Mar. 12, 2021.

(51) Int. Cl.
*A61N 1/00* (2006.01)
*A61B 5/00* (2006.01)
(Continued)

(52) U.S. Cl.
CPC ....... *A61N 1/36125* (2013.01); *A61N 1/0531* (2013.01); *H05K 1/113* (2013.01);
(Continued)

(58) Field of Classification Search
CPC ..... A61B 5/24; A61B 5/291; A61B 2562/125; A61B 5/4094; A61B 5/293; A61B 5/6868;
(Continued)

(56) References Cited

U.S. PATENT DOCUMENTS 7,905,013 B2 3/2011 Zhang et al.
8,386,007 B2 2/2013 Williams et al.
(Continued)

FOREIGN PATENT DOCUMENTS

WO 2020097305 A1 5/2020

OTHER PUBLICATIONS

Cortec, "AirRay Cortical Electrode, Product Catalogue, Electrode for Clinical Diagnostics and Research", Believed to be 2019 or earlier.
(Continued)

*Primary Examiner* — Joseph A Stoklosa
*Assistant Examiner* — Brian M Antiskay
(74) *Attorney, Agent, or Firm* — Greer, Burns & Crain, Ltd.; Steven P. Fallon

(57) ABSTRACT

A flexible electrode array with hundreds or thousands channels for clinical use includes an array of at least hundreds of electrodes on a flexible biocompatible polymer substrate. Perfusion through holes are provided through the substrate. Individual elongate leads connect to each of the electrodes, the elongate lead connections being supported by the flexible biocompatible polymer substrate and extending away from the array. Flexible biocompatible polymer insulates the individual elongate lead connections and supporting the
(Continued)

array. An interposer with individual channel connections is conductively bonded to the individual elongate lead connections. Sterile bag packaging encloses a portion of the interposer, where the outer side of the package including the array and individual elongate lead is sterile while the inner side of the packaging is non-sterile. The portion interposer inside the package is configured to connect to a circuit board within the packaging.

13 Claims, 28 Drawing Sheets

(51) Int. Cl.

| | |
|---|---|
| ***A61B 5/05*** | (2021.01) |
| ***A61N 1/05*** | (2006.01) |
| ***A61N 1/36*** | (2006.01) |
| ***H05K 1/11*** | (2006.01) |
| ***H05K 1/181*** | (2026.01) |
| ***H05K 3/32*** | (2006.01) |

(52) U.S. Cl.

CPC ............... *H05K 1/181* (2013.01); *H05K 3/32* (2013.01); *H05K 2201/041* (2013.01); *H05K 2201/10325* (2013.01); *H05K 2201/10378* (2013.01); *H05K 2203/0384* (2013.01); *H05K 2203/1305* (2013.01)

(58) Field of Classification Search

CPC ... A61B 5/685; A61B 2562/046; A61B 5/369; A61B 5/0031; A61B 5/25; A61B 5/4064; A61B 5/287; A61B 5/0006; A61B 5/6864; A61B 5/6814; A61B 5/686

USPC ................. 600/372–373, 378, 393, 544–545

See application file for complete search history.

(56) References Cited

U.S. PATENT DOCUMENTS

| | | | | |
|---|---|---|---|---|
| 8,483,794 | B2 | 7/2013 | Williams et al. | |
| 2006/0003090 | A1 | 1/2006 | Rodger et al. | |
| 2006/0224060 | A1* | 10/2006 | Garell .................. | A61N 1/0529 600/378 |
| 2008/0020566 | A1 | 1/2008 | Egitto et al. | |
| 2010/0204560 | A1 | 8/2010 | Salahieh et al. | |
| 2011/0217657 | A1 | 9/2011 | Flemming et al. | |
| 2012/0029304 | A1* | 2/2012 | Medina ................ | A61B 5/0002 600/300 |
| 2012/0231976 | A1 | 9/2012 | Wu et al. | |
| 2015/0157862 | A1* | 6/2015 | Greenberg ............. | A61B 5/293 607/116 |
| 2015/0265835 | A1* | 9/2015 | Young .................... | A61B 5/293 607/45 |
| 2015/0305643 | A1* | 10/2015 | Negi .................... | A61B 5/6846 29/854 |
| 2016/0144166 | A1* | 5/2016 | Decré ...................... | A61B 5/24 607/116 |
| 2017/0231518 | A1 | 8/2017 | Dayeh et al. | |
| 2018/0339155 | A1* | 11/2018 | Deligianni ........... | A61B 5/4836 |

OTHER PUBLICATIONS

Fang, et al., “Capacitively coupled arrays of multiplexed flexible silicon transistors for long-term cardiac electrophysiology”, Nature Biomedical Engingeering, 2017, vol. 1, No. 0038, pp. 1-12.

Gangi, et al., “Development and Translation of PEDOT:PSS Microelectrodes for Intraoperative Monitoring”, Adv. Funct. Mater., 2018, vol. 28, pp. 1-41.

Ganji, et al., “Monolithic and Scalable Au Nanorod Substrates Improve PEDOT—Metal Adhesion and Stability in Neural Electrodes”, Adv. Healthcare Mater., 2018, vol. 7, pp. 1-33.

Hong, et al., “Novel electrode technologies for neural recordings”, Nat. Rev. Neurosci., 2019, vol. 20(6), pp. 330-345.

Khodagholy, et al. “Organic electronics for high-resolution electrocorticography of the human brain”, Science Advances, 2016, vol. 2, Issue 11.

Khodagholy, et al., “NeuroGrid: recording action potentials from the surface of the brain”, Nat. Neurosci., 2015, vol. 18(2), pp. 310-315.

Kim, et al., “Dissolvable Films of Silk Fibroin for Ultrathin, Conformal Bio-Integrated Electronics”, Nat. Mater., 2010, vol. 9(6), pp. 511-517.

Kim, et al., “Flexible and Stretchable Electronics for Biointegrated Devices”, Annu. Rev. Biomed. Eng., 2012, vol. 14, pp. 113-128.

Neuralink, “Interfacing with the Brain”, 2019 or earlier.

Neuro One, “Evo Cortical Electrode”, 2019 or earlier.

Robinson, et al., “Developing Next-generation Brain Sensing Technologies—A Review”, IEEE Sensors Journal, 2019, pp. 1-13.

Shokoueinejad, et al., “Progress in the Field of Micro-Electrocorticography”, Micromachines, 2019, vol. 10, 62, pp. 1-19.

Uguz, et al., “Autoclave Sterilization of PEDOT:PSS Electrophysiology Devices”, Advanced Healthcare Materials , 2016, vol. 5, pp. 3094-3098.

Viventi, et al., “A Conformal, Bio-interfaced Class of Silicon Electronics for Mapping Cardiac Electrophysiology”, Sci. Transl. Med., 2010, vol. 2(24), pp. 1-15.

Viventi, et al., “Flexible, Foldable, Actively Multiplexed, High-Density Electrode Array for Mapping Brain Activity in vivo”, Nat Neurosci., vol. 14(12), pp. 1599-1605.

Wellman, et al., “A Materials Roadmap to Functional Neural Interface Design”, Adv. Funct. Mater., 2018, vol. 28, pp. 1-118.

Won, et al., “Recent Advances in Materials, Devices, and Systems for Neural Interfaces”, Adv. Mater., 2018, vol. 30, pp. 1-19.

International Search Report from the corresponding International Patent Application No. PCT/US2022/019778, dated Jun. 20, 2022.

* cited by examiner

1mm pitch, 32x32 array

200μm pitch, 64x16 array

150μm pitch, 32x32 array

MULTI-HUNDRED OR THOUSAND CHANNEL ELECTRODE ELECTROPHYSIOLOGICAL ARRAY AND FABRICATION METHOD

PRIORITY CLAIM AND REFERENCE TO RELATED APPLICATION

The application claims priority under 35 U.S.C. § 119 and all applicable statutes and treaties from prior U.S. provisional application Ser. No. 63/160,107, which was filed Mar. 12, 2021.

STATEMENT OF GOVERNMENT INTEREST

This invention was made with government support under EB029757 awarded by the National Institutes of Health and under CMMI1728497, 1351980, and ECCS1542148 awarded by the National Science Foundation. The government has certain rights in the invention.

FIELD

Fields of the invention include electrophysiological recording and stimulation of biological tissue composed of excitable cells. Example applications of the invention include but are not limited to wearable neuromodulation devices, implantable devices for brain-machine interfaces, implantable devices for therapeutic applications, implantable devices for functional mapping during surgical resection operations where identification and delineation of boundaries for diseased and eloquent tissue is needed. One example of such operations is the awake neurosurgical mapping in patients with brain tumors or epilepsy. The fields of invention can also be used in closed loop neuromodulation devices in brain, spinal, and peripheral nerve implants, cardiac pacemakers, and a variety of other electrophysiology and electrochemical sensors and stimulators that can generally interface with human tissue above or below the skin surface.

BACKGROUND

Electrical recording and stimulation of the human brain are critical tools for effective clinical intervention in an increasing range of neuropsychological diseases and disorders. Mapping can be accomplished with passive recordings where pathological neurophysiological event recordings can identify pathological tissue. Stimulation mapping can also be performed to identify and preserve eloquent tissue, for example by disrupting function for motor mapping. These electrophysiological implants form the basis of bioelectronic medicine with the nervous system, where bi-directional (record and stimulate) interfaces enable closed-loop autonomous systems which can provide automated therapy. The technology for clinical recordings and stimulation have changed little in the last several decades, and it is widely recognized that higher spatiotemporal resolution, more flexible and more sensitive electrode systems are needed.

Currently, the primary tool in clinical use is the electrocorticography (ECoG) array which is typically based on stainless steel (SST), platinum (Pt), or platinum iridium (PtIr) electrodes embedded in flexible silicone sheets for application to the surface of the brain. Additionally, electrodes have been implanted into the brain tissue where Pt or SST contacts are embedded in polyurethane tubing that is generally 0.8 mm-1.2 mm in diameter. This type of electrode is called a depth electrode and it enables deeper structures to be interrogated through a technique called stereoelectroencephalography (sEEG).

Electrodes are placed in the operating room either via open craniotomy for surface grid and strip electrodes (ECoG), or via twist drill holes for depth electrodes (sEEG). Currently, the detection resolution of disordered tissues or functional boundaries is limited by the large contact size and spacing of the intracranial electroencephalography (iEEG), and this anatomical and physiological imprecision necessarily limits the precision of the curative surgery.

Adtech Medical, Natus, and Integra all commercialize ECoG grids with different schemes for contact arrangement. These contacts are generally made of Pt, PtIr, or SST, and are pressed in a silicone film that is about 0.5 mm thick. They are usually 1 cm spaced, though custom-made higher density grids (256 channels, 4 mm pitch, 1.17 mm electrode diameter, coverage area of 6.4 cm×6.4 cm) are available. Blackrock Microsystems is also commercializing ECoG arrays that, according the company's website, are up to 50% thinner than comparable products, require a fewer number of cables, and with variable diameter sizes from 0.3 mm-0.7 mm. The limitations of these handmade grids with contact pressing and wire soldering on the back of the contact are well known to limit their scalability to large numbers of contact and to tight contact spacing.

Cortec commercializes under FDA market clearance 1×4 and 8×8 AirRay® Cortical Electrodes. These electrodes are built on multi-layer silicone and parylene C on which a PtIr foil is placed and cut using a laser for the formation of contact pads and connectorization leads on the grid. The PtIr layer is then embedded in another silicone layer where only PtIr contacts are exposed. Two cables provide connectorization to all 64 contacts. This manufacturing technique allow flexibility in design and machining contacts with variable sizes but does not permit the scalability of the contacts to hundreds of channels, limited by the resolution of laser writing that is typically of the order of 200 μm for industrial applications.

NeuroOne Inc. is developing a thin-film electrode technology that is built on top of 25 μm thick polyimide layers. The product is referred to as the Evo® Cortical Electrode. The product includes a single thin tail design with two rows of electrodes.

Existing approaches for increasing the channel count involved the integration of integrated circuits on the electrodes to facilitate wiring and reduce the wire count from the electrode itself to the outer world. Extensive efforts were employed in the transfer of Si transistors on flexible substrates.

Neuralink has successfully adopted conventional flip-chip bonding techniques to form interconnects between custom CMOS chips and polymer-based electrode threads. This approach shows significantly improved channel count over the clinical standard. Systems are capable of recording and wirelessly transmitting 'spikes' from up to 3072 channels. Due to the packaging and integration, this system is presently incapable of recording and wirelessly transmitting broadband activity. See, Musk, E. An integrated brain-machine interface platform with thousands of channels. Journal of medical Internet research 21.10 (2019): e16194.

Obaid et al. describe a method of mechanically bonding microwire bundles to CMOS chips for ultra-high channel count neurophysiological recording. This approach involves bundling and casting glass-insulated microwires in medical-grade epoxy, then polishing and etching the ends to expose the metal interconnects. Once exposed, the method mechanically crimps and bonds these wires to planar CMOS arrays without the need of precisely aligning each interconnect to each CMOS pad. The described approach demonstrated mechanically robust and long-lasting interconnect yields in the range of 90% or greater with minimal increases in noise. See, Obaid, Abdulmalik, et al. Massively parallel microwire arrays integrated with CMOS chips for neural recording. Science Advances 6.12 (2020): eaay2789. Paradromics is commercially developing this technology in a package that supports up to 65536 channel recordings in parallel for use in therapies to treat brain disorders. Successful clinical implementation has not yet been demonstrated.

Dayeh et al. WIPO Publication No. WO2020097305A1 discloses a method for fabricating a Pt nanorod electrode array sensor device including formation of planar metal electrodes on a flexible film, co-deposition of Pt alloy on the planar metal electrodes via physical vapor deposition, and dealloying the Pt alloy to etch Pt nanorods (PtNRs) from the deposited Pt alloy. PtNRs are capable of sensing, stimulating or inhibiting the neurological activities of excitable cells and tissue, via efficient electrochemical current exchange with surrounding tissue. Experiments demonstrated that the PtNRs create a sensor electrode having a charge injection capacity (C1C) of ~4.4 mC/cm$^2$, which is 16 times higher than that of control planar Pt films. The low impedance of the PtNR contacts (e.g., at 1 kHz 16.89±0.47 kOhm for a diameter of 30 μm) allowed recording of local field potentials as well as action potentials (APs) of single neurons from the cortical surface. The recorded APs demonstrate the quality on par with that recorded from beneath the cortical surface—that is inside the brain tissue—using depth electrodes. The PtNR microelectrode merits, such as high yield, high stability, low electrochemical impendence, high density, high sensitivity, high effective/geometric surface area (ESA/GSA) ratio, minimally destructive to brain tissue (thin layer placed on the cortical surface) and biocompatibility, etc., enable the PtNR microelectrodes to advance sensing to aid the next generation clinical neurotechnologies to be capable of recording and stimulation of excitable tissue including the brain, spinal cord, and peripheral nerves at ensemble, single or multi-unit activity for application in functional mapping neurosurgery, neuroprosthesis, pain management, pace makers, etc.

Dayeh et al. US Patent No. US20170231518A1 discloses conformal penetrating multi electrode arrays. A plurality of penetrating semiconductor micro electrodes extends away from a surface of a flexible substrate and are stiff enough to penetrate cortical tissue. Electrode lines are encapsulated at least partially within the flexible substrate and electrically connected to the plurality of penetrating microelectrodes. The penetrating semiconductor electrodes can include pointed metal tips. The pointed metal tips are formed by some consumption of silicon during an etching process and coating with metal. The pointed metal tips are micrometer scale in diameter (much greater than 100 nm in diameter) and hundreds of micrometers long to penetrate the brain to the targeted cortical depth. These electrodes measure extracellular activity from intact brains, and even in the depth of mini-brains.

SUMMARY OF THE INVENTION

A preferred flexible electrode array with hundreds or thousands channels for clinical use includes an array of at least hundreds of electrodes on a flexible biocompatible polymer substrate. Perfusion through holes are provided through the substrate. Individual elongate leads connect to each of the electrodes, the elongate lead connections being supported by the flexible biocompatible polymer substrate and extending away from the array. Flexible biocompatible polymer insulates the individual elongate lead connections and supporting the array. An interposer with individual channel connections is conductively bonded to the individual elongate lead connections. Packaging encloses a portion of the interposer, where the outer side of the package including the array and individual elongate lead is sterile while the inner side of the packaging is non-sterile. The portion of interposer inside the packaging is configured to connect to a circuit board within the packaging.

A preferred method for fabricating a flexible electrode array with hundreds or thousands of channels for clinical use includes providing a rigid carrier substrate. A release layer is deposited on the carrier substrate. A first thin flexible layer of non-conductive biocompatible polymer is deposited on the release layer. A pattern is formed of elongate metal leads and electrode sites and pad sites at opposite terminal ends of the metal leads. Electrochemically active material is deposited on the electrode sites. An etch stop layer is formed on the electrochemically active material. A second thin flexible layer of non-conductive biocompatible polymer is deposited over the pattern. A mask is deposited and patterned with openings at the electrode and pad connector sites and at perfusion sites adjacent the electrode sites. Etching is conducted to open vias to the etch stop layer at the electrodes sites and through the first and second thin flexible layer at the perfusion sites to create perfusion holes. The mask is removed. The flexible electrode array is released from the carrier substrate.

BRIEF DESCRIPTION OF THE DRAWINGS

FIGS. 2T-2GG are cross-sectional schematic diagrams illustrating the preferred method for fabricating multi-hundred or thousand channels electrode array;

DETAILED DESCRIPTION OF THE PREFERRED EMBODIMENTS

Figure 1A:
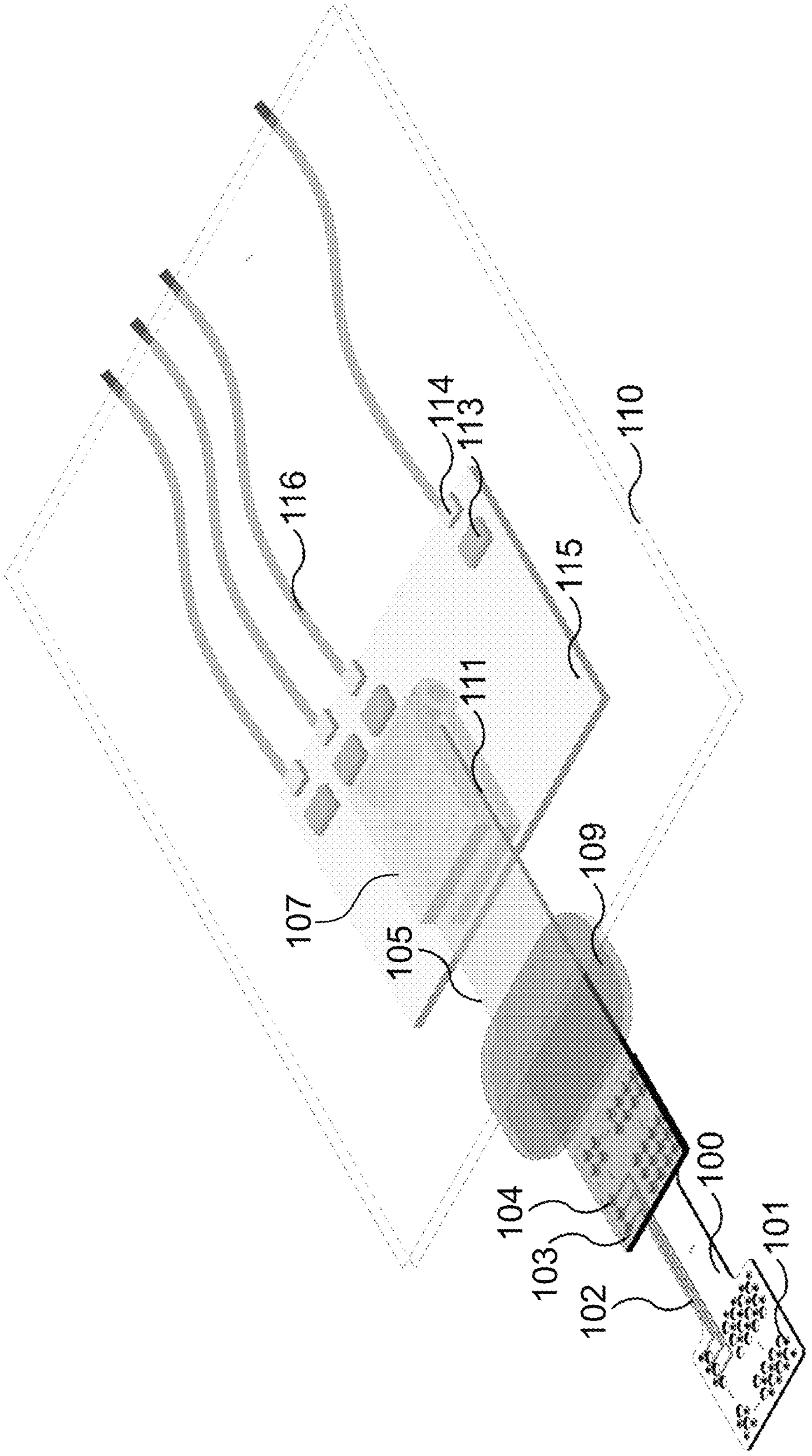
FIG. 1A is a schematic perspective diagram of a preferred embodiment multi-thousand channels electrode array of the invention.

A preferred fabrication method provides a scalable fabrication process for production of multi-hundred or thousand channels, high-density, and highly electrochemically active sensing and stimulating electrode arrays on large area glass plates (for example 2"×2" and preferably 7"×7" or more), Si substrates (for example 4" and preferably ≥8"), or any other suitable carrier substrate that is temporarily used to complete the microfabrication steps. Semiconductor fabrication processes can therefore be used to form electrode sites and leads, while preferred arrays can also have a sensing area that is many centimeters distant to non-sterile acquisition and stimulation circuitry. The multi-hundred or thousand channel electrode arrays provided by the invention enable higher spatial resolution over broader areas compared to prior technologies when used as a cortical array. Arrays of the invention can support greater spatial localization of neurophysiological activity, thereby improving respective boundaries in advanced neurosurgeries.

A preferred method for using an array of the invention provides recording and stimulation of hundreds or thousands of channels on the patient's tissue in the operation room employing sterilizable flexible electrodes, rigid extended interposers, and amplification board with compact, high-density socket. A major advantage of preferred arrays is the physical separation of sterilized implant from acquisition circuitry, because this characteristic enables facile clinical translation in a commercially viable package. The application of the electrode system is suitable for use on humans and lower animal species.

The electrochemically sensitive electrode in preferred arrays of the invention include Pt nanorods or poly(3,4-ethylenedioxythiophene) polystyrene sulfonate (PEDOT:PSS) that are capable of sensing, stimulating or inhibiting the electrophysiological activities of the neurons, cardiomyocytes, nerve, muscle or any other excitable cells and tissue, via efficient electrochemical current exchange with surrounding tissue. Other electrochemically active materials can be used. Examples include Pt or Pt nanorods, Au, poly(3,4-ethylenedioxythiophene) polystyrene sulfonate (PEDOT:PSS), Si, Carbon nanostructures, or any other biocompatible material with low electrochemical impedance.

Preferred fabrication methods provide reliable connection of hundreds or thousands of channels of fine metal electrodes (e.g., length over 7" long, a few μm wide, and pitch below 10 μm) on a flexible polymer film. Experiments provided a high yield (>99%) of functional channels using standard neural probe manufacturing methods, for in-vivo neural recording applications.

Experiments demonstrated that the invention provides a scalable and monolithic integration method for the fabrication of high yield Pt nanorods and PEDOT:PSS-based micro-electrode arrays with excellent electrochemical properties and that are built on an ultra-thin flexible polymer such as parylene C or polyimide, or any other flexible biocompatible polymer.

A preferred method for fabricating multi-thousand channel electrode array sensor/stimulator device includes forming planar metal electrodes on a flexible film, depositing electrochemically active materials on the planar metal electrodes via physical vapor deposition, spin-coating or electrochemical deposition. The method includes using a release layer on a carrier substrate, preferably an anti-adhesion layer, depositing the flexible film on the anti-adhesion layer, patterning the flexible film for the planar metal electrodes and electrode leads, depositing the planar metal electrodes and electrode leads, depositing an additional flexible biocompatible polymer layer on the planar metal electrodes. Selectively etching is conducted on the additional flexible biocompatible layer over electrode sites to expose the electrode sites, and to form perfusion holes adjacent the electrode cites. Electrochemically active material is deposited at electrodes sites. The flexible film can be peeled from the carrier substrate.

A preferred electrochemically sensitive electrode sensor device includes either a plurality of porous Pt nanorods or PEDOT:PSS on a planar metal electrode forming a sensor electrode. The planar metal electrode is on a flexible substrate. Perfusion holes are adjacent the sensor electrodes. An electrode lead on the flexible substrate extends away from the planar metal electrode. Insulation is around electrochemically active material an upon the electrode lead. The Pt nanorods on the planar electrodes can be polycrystalline Pt, or any form of structurally stable Pt material that does not dissociate with electrochemical cycling. A preferred flexible substrate is parylene C, with a preferred thickness of ~2-20 μm.

A preferred method to bond the multi-thousand channels flexible electrode array with the extended interposer include depositing a conducting epoxy on top of the contacts of the extended interposer, temporarily placing the multi-hundred or thousand channel flexible electrodes on a glass carrier substrate, aligning the flexible electrode with the extended interposer, and bonding them together applying heat and pressure. The interposer is preferably a rigid extended interposer that is sterilizable by conventional medical autoclave sterilizers. A preferred rigid extended interposer includes multilayer printed circuit boards that are compatible with medical grade autoclave, ethanol oxide, aerosolized hydrogen peroxide, ultraviolet or gamma radiation, or other sterilization techniques. The bonding material is conductive material, e.g. soldering paste, solder balls, or anisotropic conductive film. Conductive epoxy, solder, or anisotropic conductive films are preferred to form the bonding interface between the flexible electrode and interposer. The connection step can establish reliable (>99%) and quick (a few seconds) one touch electrical connection between thousands of sensing electrode array and the acquisition board using a compact (<5 cm), high-density socket (>100 pins/$cm^2$) with thousands of contacts. The interposer can include a land grid array (LGA), ball grid array (BGA), or pin grid array (PGA) at an opposite end, which can be pressed against an acquisition circuit board. Hermetic sealing between sterile and non-sterile regions for use in the operating room can be established around the rigid extended interposer board.

Preferred embodiments of the invention provide a method for the scalable fabrication and connection of a multi-hundred or thousand channel electrode array for clinical recording and stimulation of excitable tissue in vivo. With large rectangular glass substrates (≥7"×7") or large diameter Si wafers (≥8") as the carrier substrate, multiple arrays can be formed on the same carrier and released, and then each can be attached to an interposer board, sterilized and sealed. This allows rapid prototyping and fabrication of custom, modular, and patient-based arrays where the contact coverage (e.g., 1 mm-10 cm) and spacing (e.g., 30 μm-1 cm) can be customized.

A preferred electrochemically sensitive recording and stimulating electrode material includes a plurality of porous Pt nanorods, PEDOT:PSS, or any electrochemically sensitive electrode material with low impedance per unit area, on a planar metal electrode. The planar metal electrode is formed on a flexible substrate. An electrode lead on the flexible substrate extends away from the planar metal electrode towards the connector bonding region. A second insulation layer surrounds these leads and limits the electrochemical interface to the surface of each channel's electrochemically active material. A preferred flexible substrate is parylene C, with a preferred thickness of 2-20 μm.

Preferred embodiments of the invention will now be discussed with respect to the drawings. The drawings may include schematic representations, which will be understood by artisans in view of the general knowledge in the art and the description that follows. Features may be exaggerated.

FIG. 1A shows multi-hundred or thousand channel flexible electrode array with electrochemically active microelectrodes 101. The flexible electrode array preferably includes a Cr/Au film (conductive layers) 102, though other combinations of an adhesion metal layer (e.g. Ti) and highly conductive layer (e.g. Pt) or other single or multiple metal layers. Parylene C layers or other inert thin, flexible and biocompatible polymer layers 100 passivate the device surface. The polymer layers 100 include openings through which the microelectrodes 101 extend and openings for perfusion holes. The Cr/Au conductive films 102 have a typical thickness of 100-10,000 nm. These thicknesses can be adjusted based on device design considerations and require current carrying capacity for stimulation. The electrochemically active materials 101 have a typical thickness of 200 nm-2,000 nm, to tailor the electrode impedance and charge capacity depending on geometrical restrictions and the application requirements. The electrode diameter 101 and the contact side-to-side spacing can differ from micron to millimeter scale depending on application. The passivation parylene C layers 100 have a thickness of ~0.5-3 μm. Metal leads 102 are covered by passivation parylene C layer 100 to prevent signal shunting and minimize crosstalk between adjacent electrodes. The metal contacts/leads, 101, 102, and 103 are preferably patterned by photolithography but could be also be patterned by other techniques including electron-beam lithography, nano-imprint lithography, electron beam lithography, etc.

FIG. 1A illustrates how the microelectrode probe is electrically conducted from electrochemically active surface 101 to Au/Cr metal leads 102, peripheral Au metal pads 103, conducting epoxy 104, extended interposer 105, high-density socket 111, and an acquisition board 115. The position and role of conducting epoxy 104 (211 in FIG. 2O) are illustrated more clearly in FIG. 2O. It is used to make electrical and mechanical connection between the extended interposer 208 and metal leads 103.

FIG. 1A illustrates how a hermetic sealing in made across the rigid extended interposer using a sterile plastic bag 110 and sterile hermetic sealing tape 109. Across the hermetic seal, the outer region of 110 is considered sterile zone and inner region of 110 is considered non-sterile zone. Inside the non-sterile zone, an acquisition board 105 populated with amplifier chips 113 and digital input/output pins 114, pre-connected with the digital cables 116 are inserted, and compact socket 111 and the latch 107 are used to connect the extended interposer with the acquisition board 105.

Figure 2A:
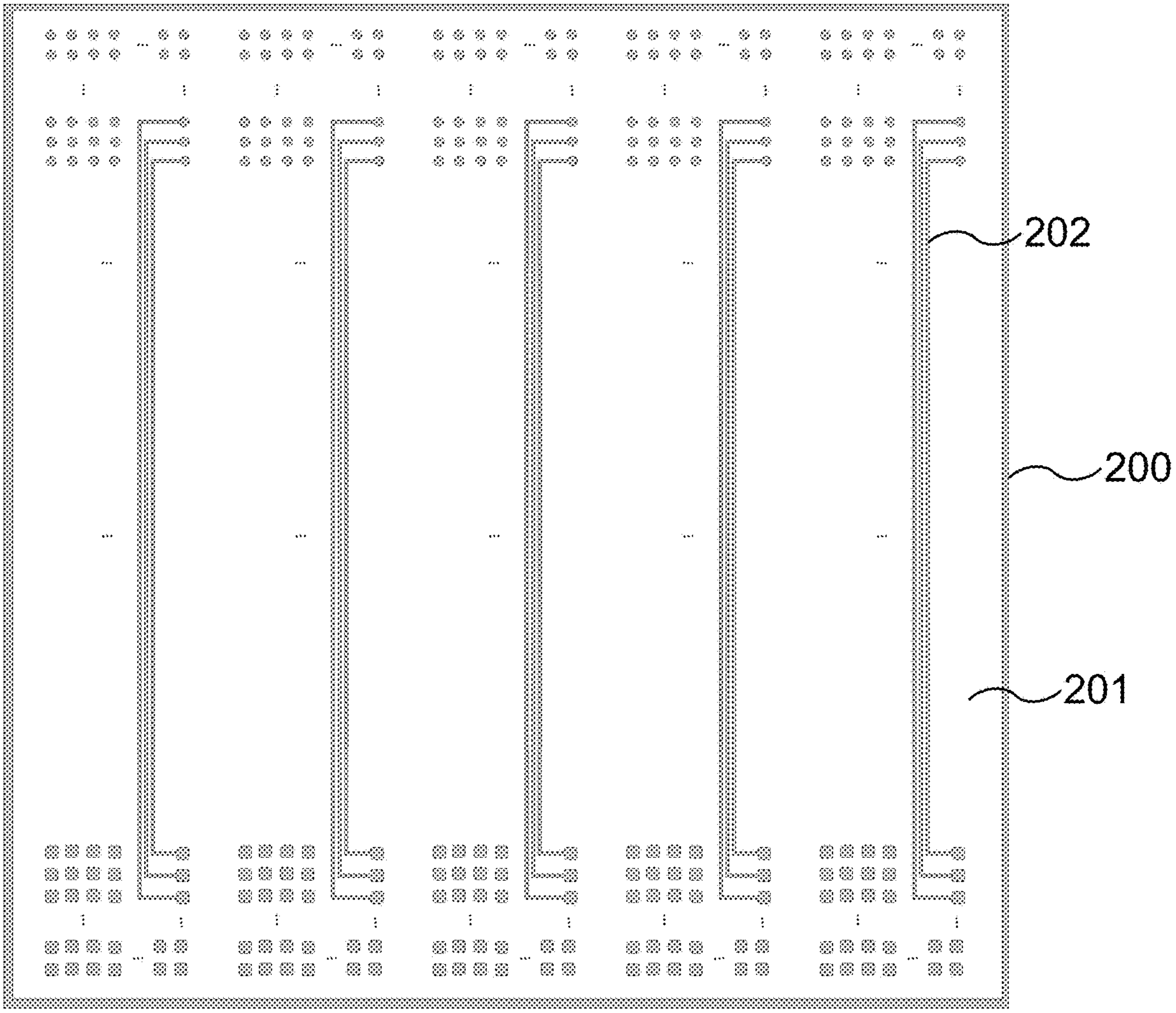
FIGS. 2A-2E are schematic top-view diagrams illustrating a preferred method for fabricating multi-hundred or thousand channels electrode array.
Figure 2B:
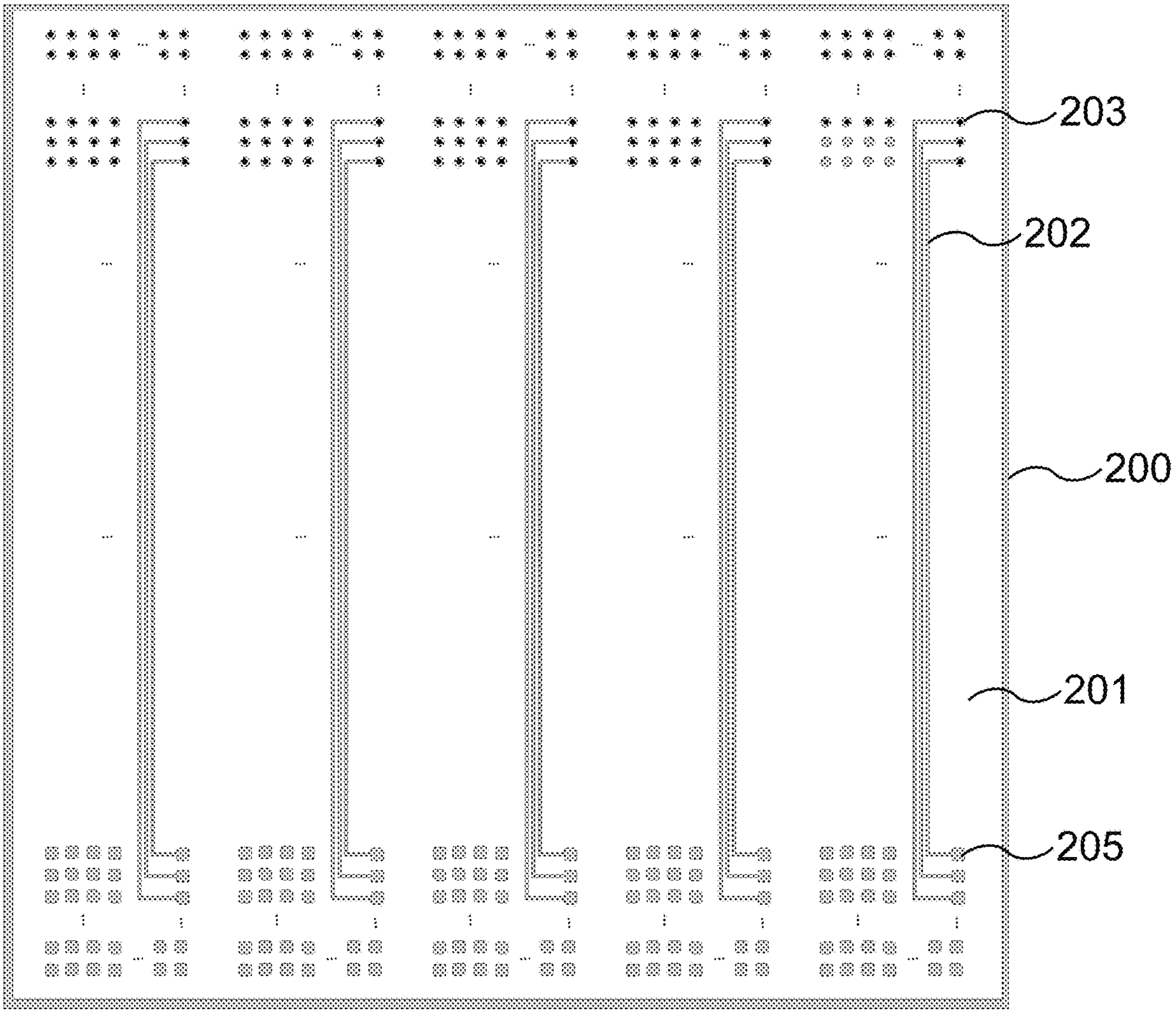
Figure 2C:
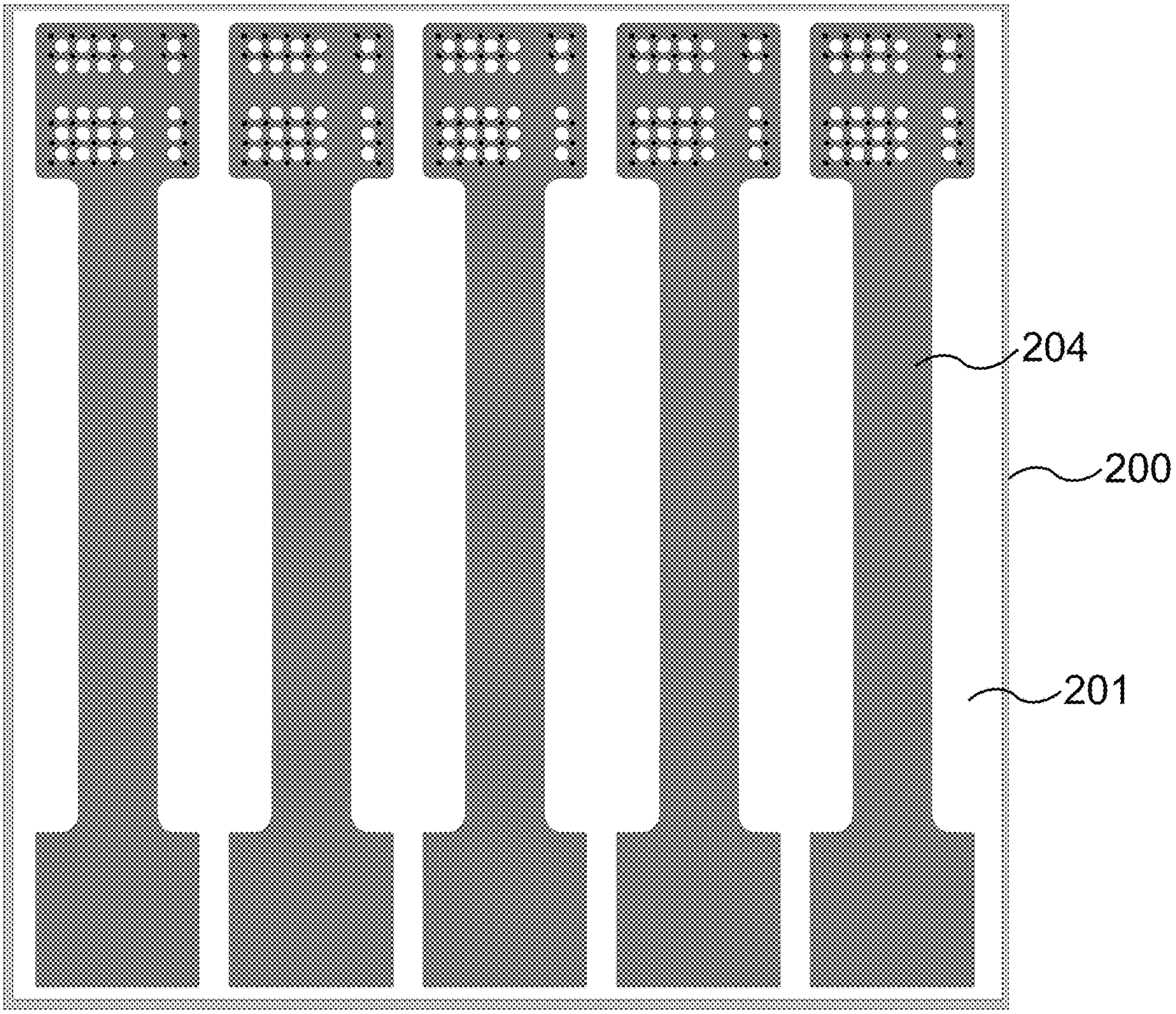
Figure 2D:
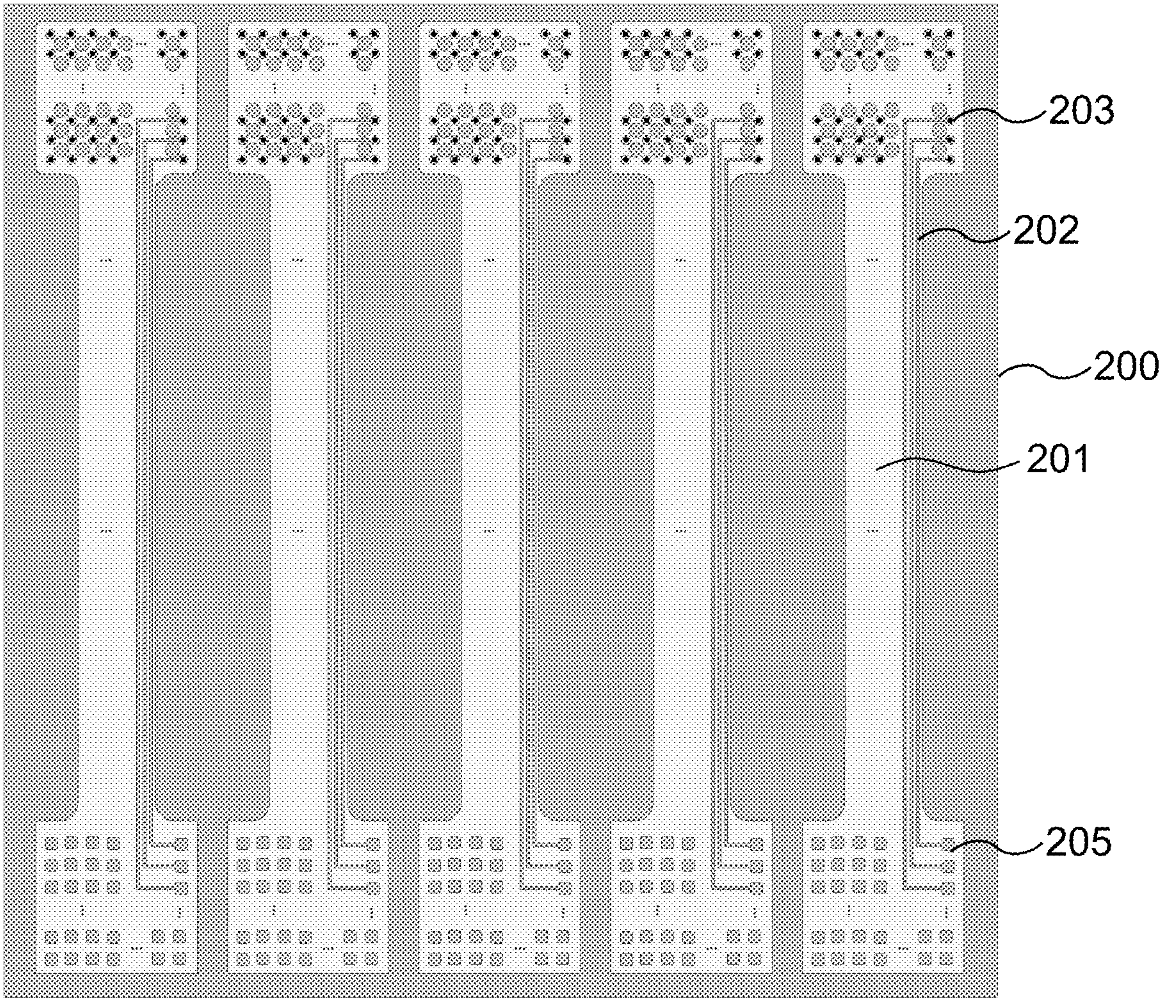
Figure 2E:
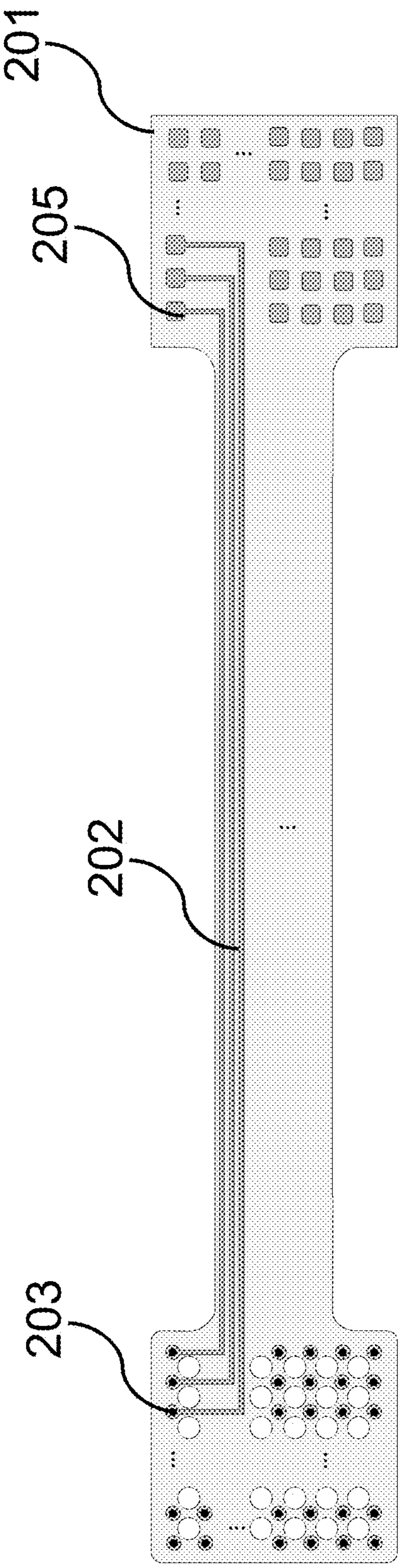
Figure 2F:
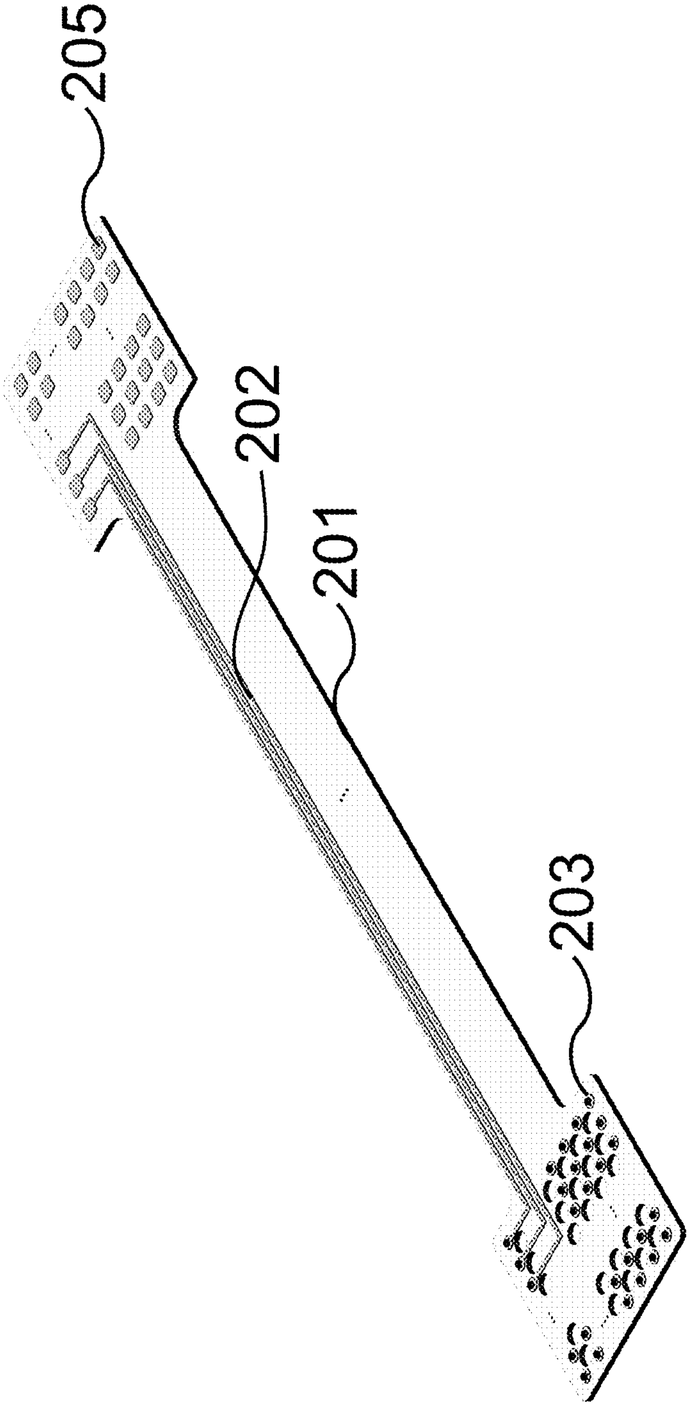
FIGS. 2F-2K are schematic perspective diagrams illustrating a flexible electrode array and extended interposer, and a preferred method for bonding them together.

FIGS. 2A-2F illustrate the multi-hundred thousand channel array fabrication procedures for the FIG. 1A device, showing 5 devices being formed on a single carrier substrate. In FIG. 2A, a large area (multiple inches×multiple inches) (e.g., over 7"×7", but at least 2"×2") glass or other rigid material substrate 200 serves as carrier substrate for the five arrays is first solvent cleaned. Then, diluted Micro-90 (0.1%)—an anti-adhesion layer 207 (see FIG. 2L) is spun-cast on the glass substrate 200 to facilitate the separation of the device from the carrier substrate after device completion. Then a first non-conductive biocompatible polymer layer, e.g., parylene C layer 201, is deposited on glass substrate 200. Next, Au/Cr or other metal lead/electrode sites 202 are deposited and defined by lithography and deposited using standard metal deposition techniques. In FIG. 2B, this patterning creates a pattern of elongate metal leads electrode 203 and pad 205 sites at opposite terminal ends of the metal leads. Electrochemically active material is formed on top of the electrode sites 203, and can advantageously serve as an etch stop layer. On top of the all these structures, second non-conductive biocompatible polymer layer, e.g., parylene C layer, is conformally coated to passivate the metal leads. FIG. 2C shows deposition of 50-nm-thick Ti hard mask 204 on top of the metal electrodes to define the outlines and perfusion holes (see FIG. 2C) on the parylene C film. Mask 204 could be another material, e.g., Cr. FIG. 2D shows dry etching of parylene C film 201 through Ti hard mask 204 to expose the electrode sites and then removing Ti hard mask 204 by chemical etching. FIG. 2E illustrates a flexible electrode array released from the substrate, e.g., by dissolving the anti-adhesion layer 207 (see FIG. 2L). Other methods of release include mechanical peeling, chemical etching of the substrate, or capillary action in the electrode/substrate interface. Perspective view of released flexible electrode array is shown in FIG. 2F.

Figure 2G:
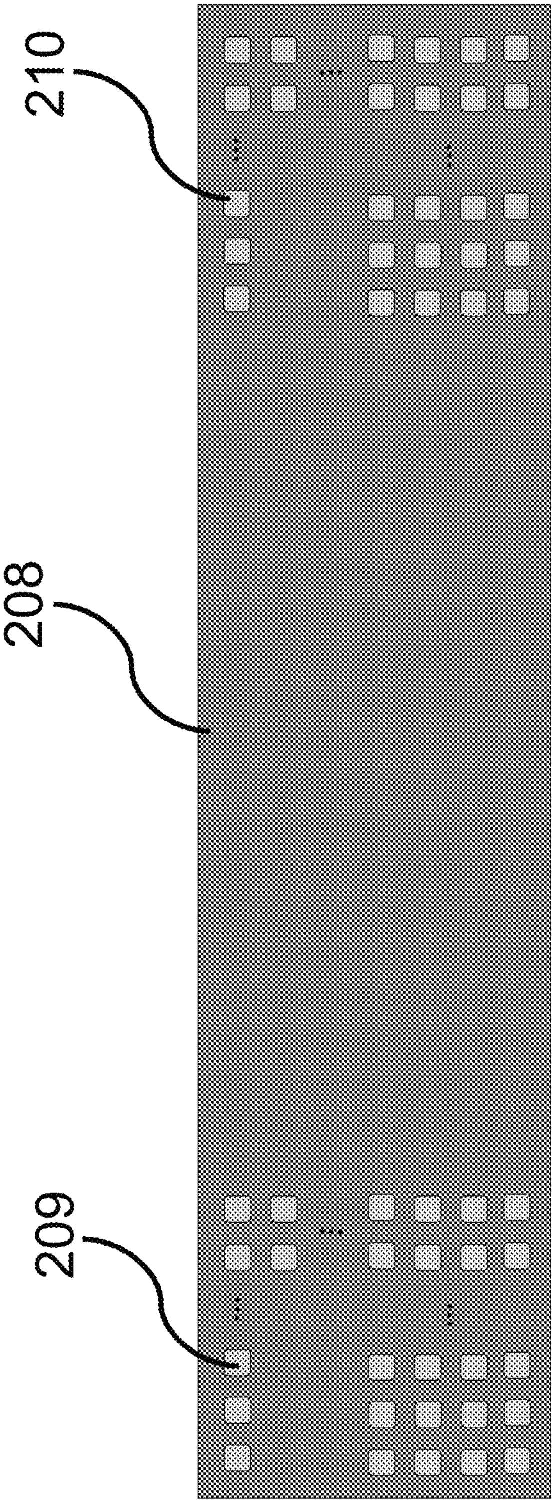
Figure 2H:
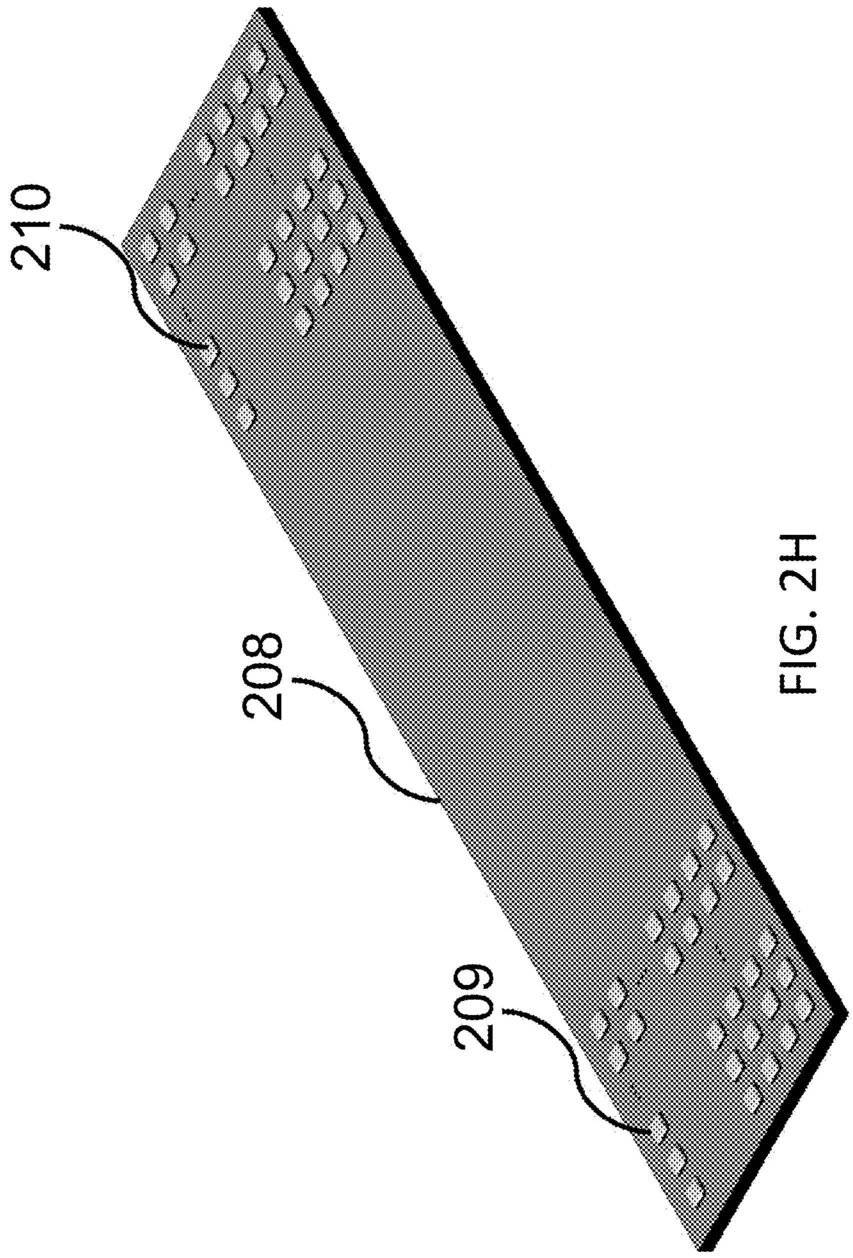
Figure 2I:
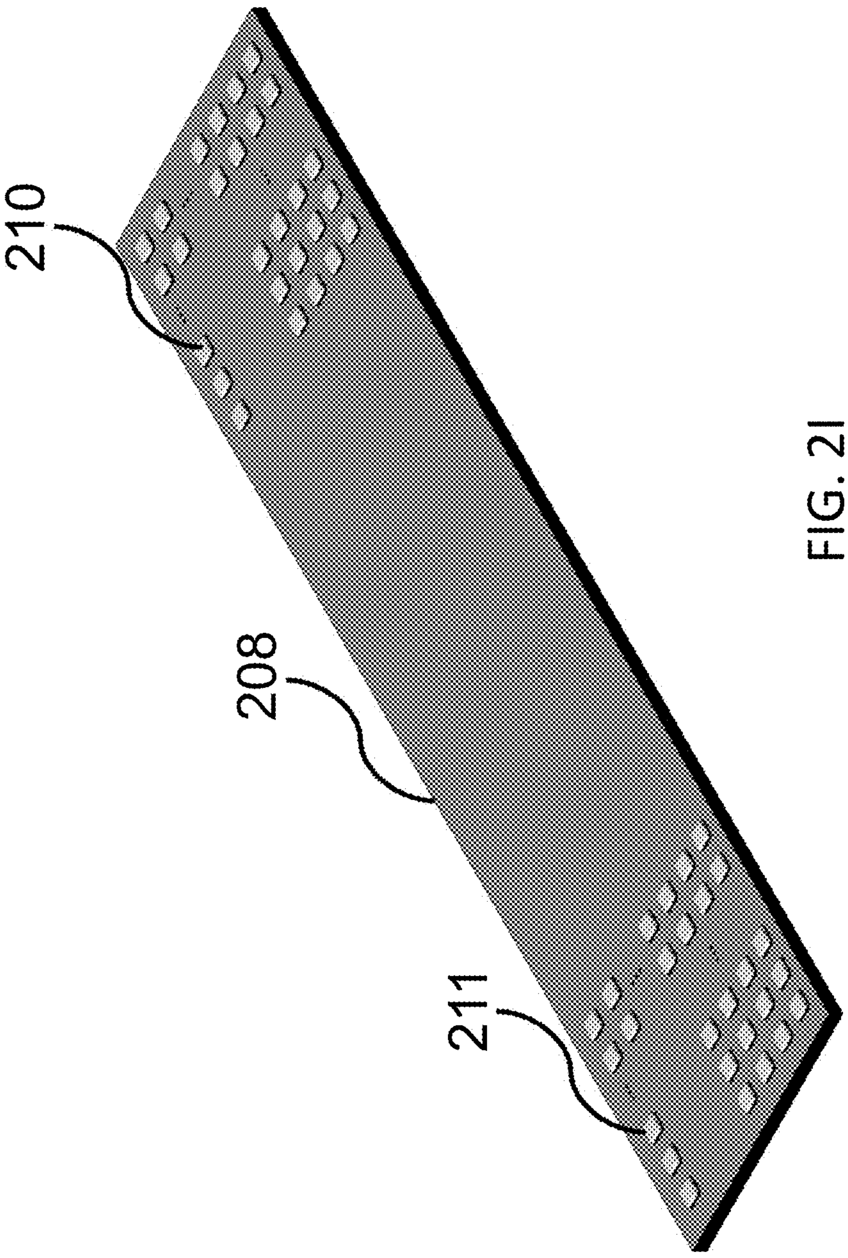

FIGS. 2G and 2H show top-view and perspective-view of an extended interposer that are made of a multilayer printed circuit board 208 which comprises of high-density contacts 209 and 210 on each end of the board and high-density metal traces embedded in multiple layers of FR4.

Figure 2J:
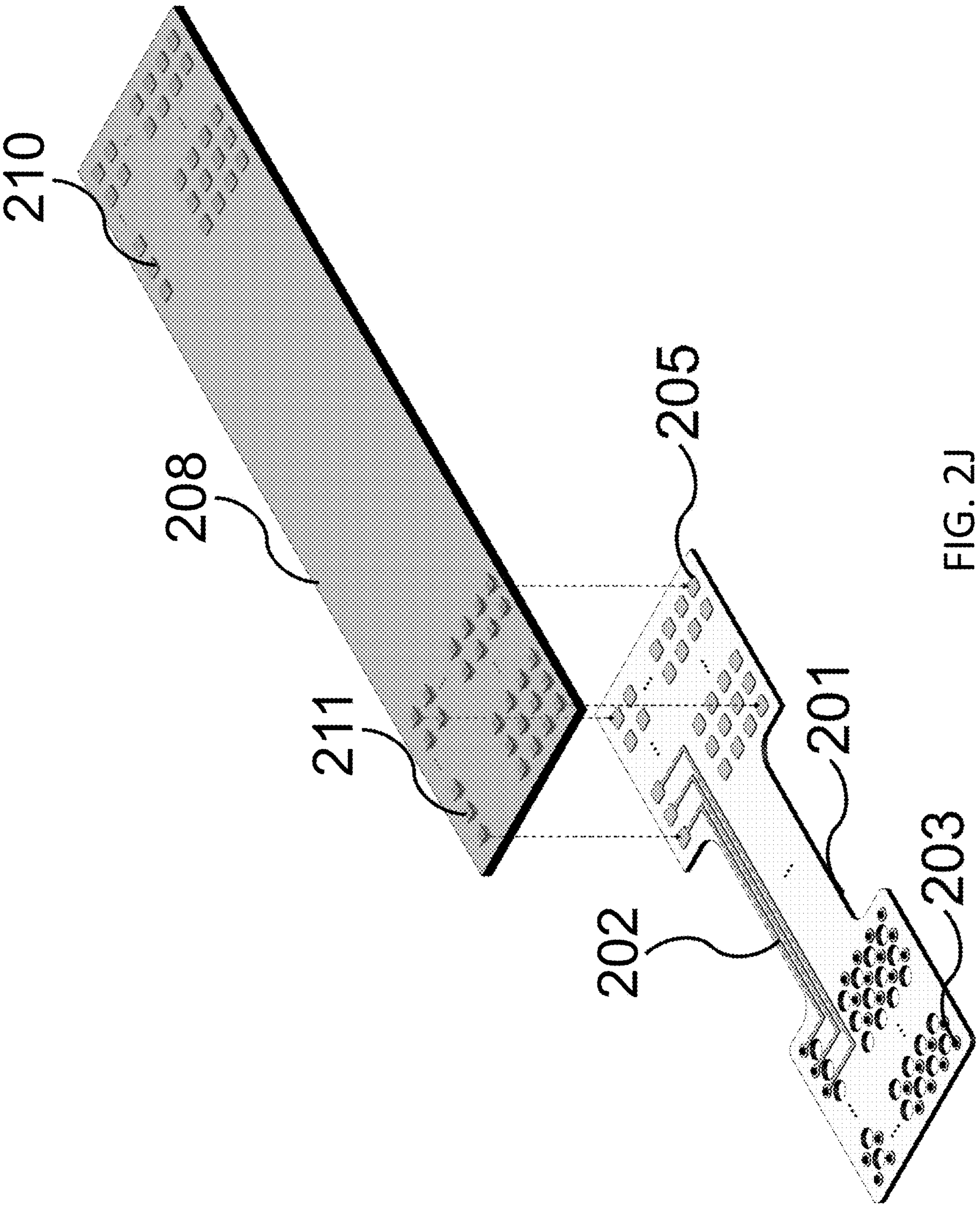
Figure 2K:
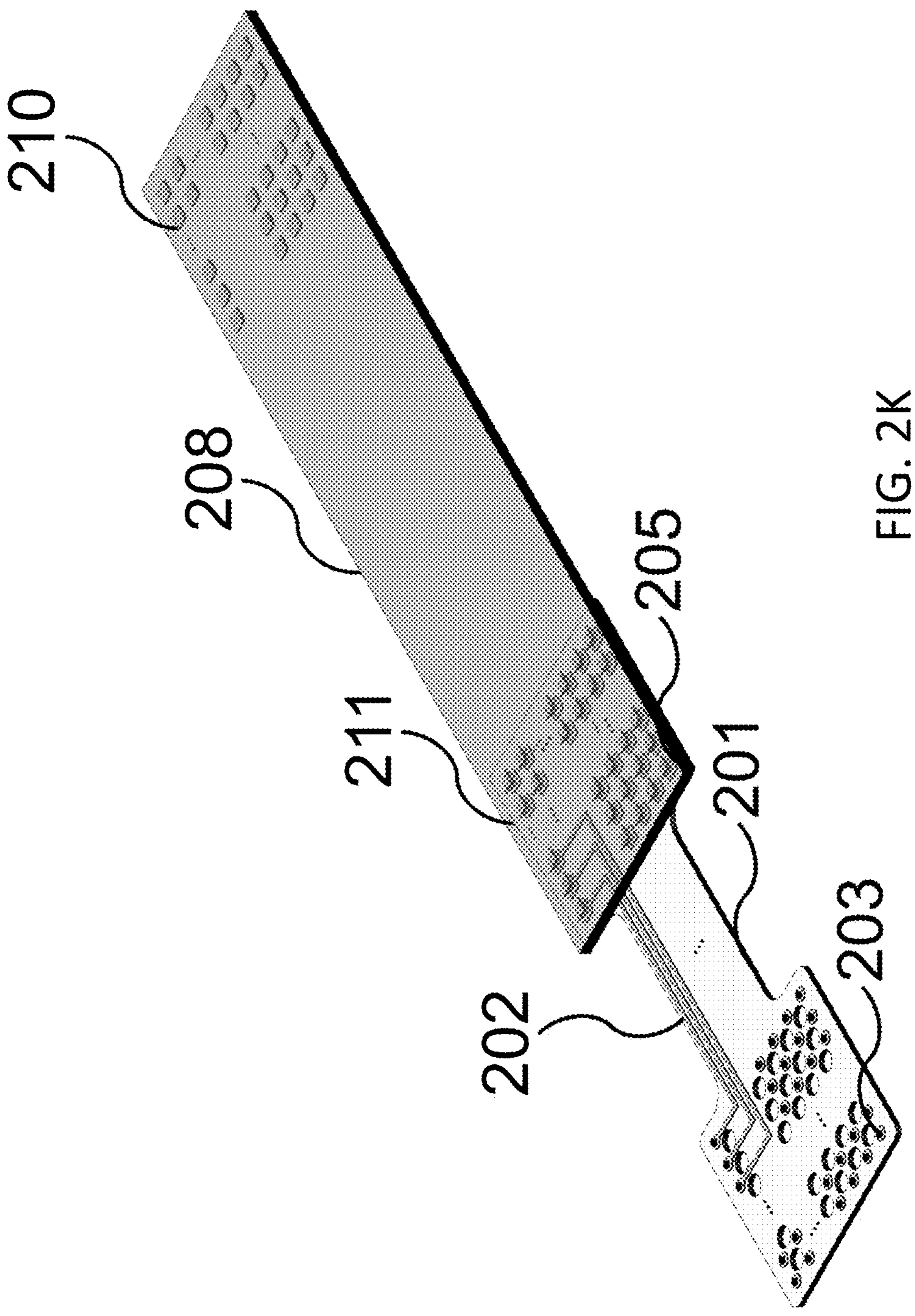
Figure 2L:
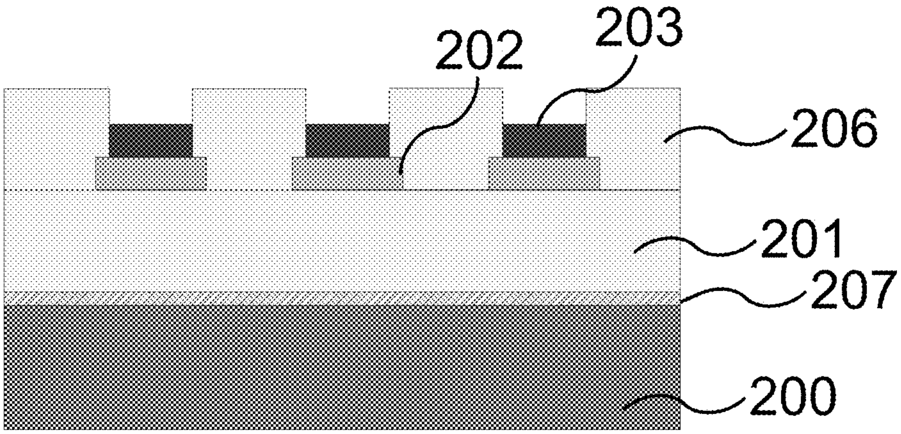
FIGS. 2L-2O are schematic cross-sectional diagrams illustrating a preferred method to release the flexible electrodes and make the conducting bonding interface.
Figure 2M:
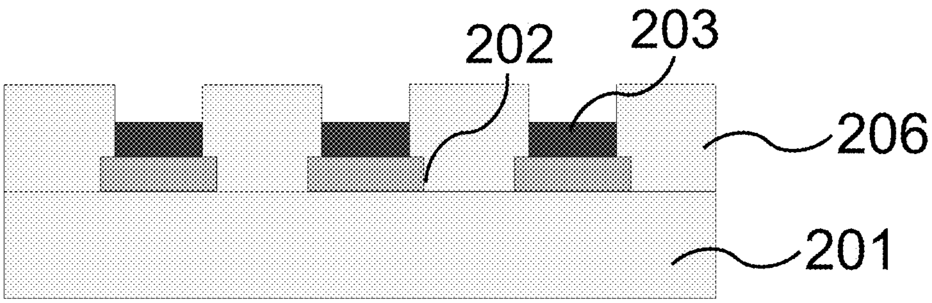
Figure 2N:
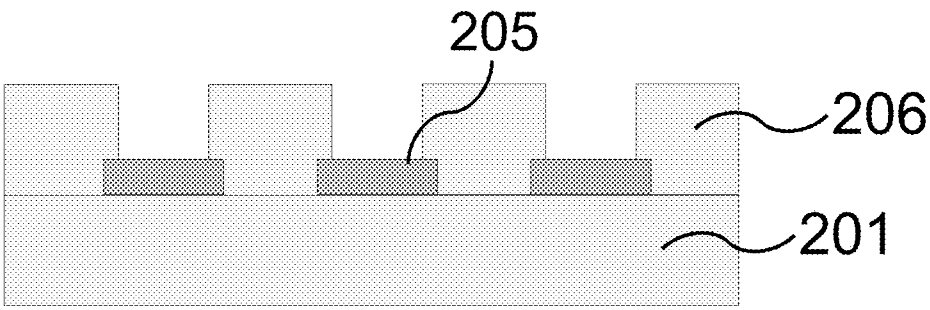

FIGS. 2I-2O summarize the steps to bond the flexible electrode array on the rigid extended interposer board. FIG. 21 shows conductive epoxy 211 deposited on top of individual contact pads of the extended interposer. Extended interposer board is bonded with the contact pads of flexible electrode array 205 in a micro-alignment stage as shown in FIG. 2J and bonded using heat and pressure as shown in FIG. 2K, and sealed with the second polymer layer 206. The electrode illustrated in FIG. 2K is sterilizable by medical grade autoclave sterilizer. Cross-sectional schematics in FIG. 20 shows how the alignment between the pads on flexible electrode array 205 and contacts on the interposer 209 are made, and the conductive epoxy 211 squeezed between the contacts ensures reliable conductive connections between them.

Figure 2O:
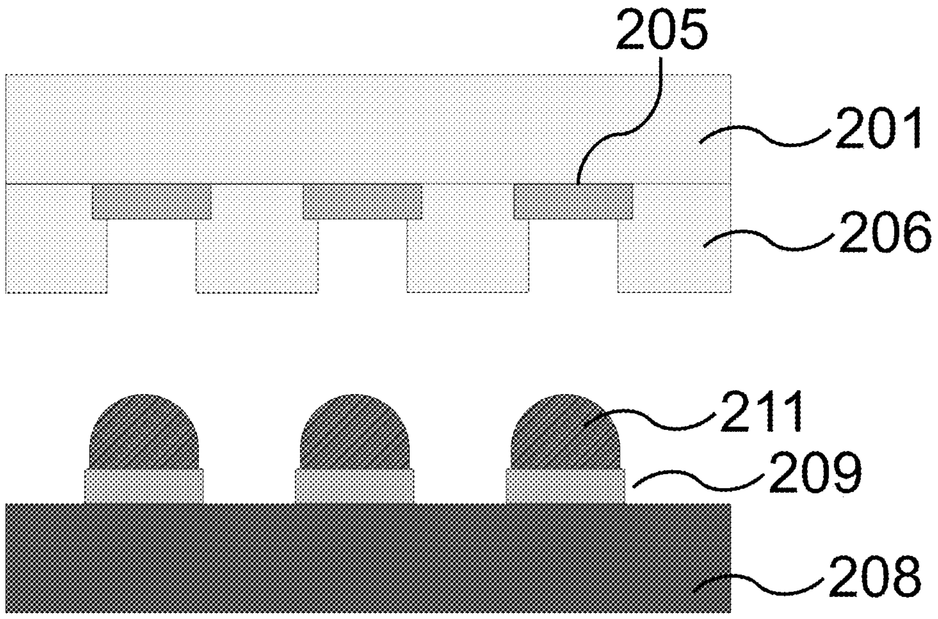

The alignment occurs in FIG. 2O by micro-alignment stages with four-axis degrees of freedom that could precisely align the microelectrode (that is temporarily placed on glass plate) and the extended interposer. Once aligned and placed in contact, the microelectrode and extended interposer board are thermally cured to ensure reliable electrical and mechanical connection across all bonding contacts. Flip-chip bonder could be used to automate the alignment and bonding process.

Figure 2P:
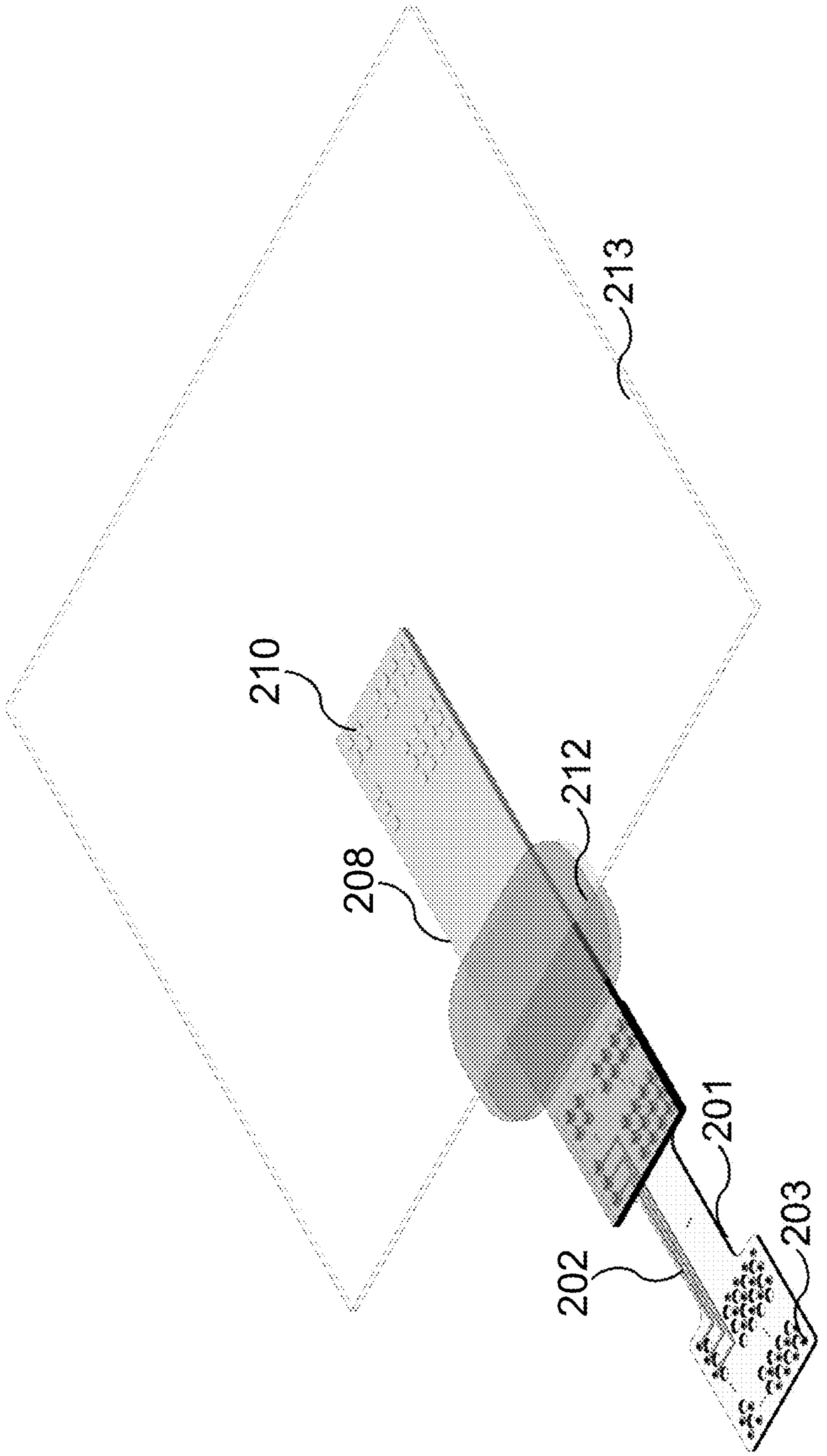
FIGS. 2P-2S are schematic perspective diagram illustrating a preferred method to set up the multi-thousand channels electrode array in the operation room using sterile bag, hermetic sealing tapes, and the acquisition board with a high-density socket.

FIG. 2P illustrates how a hermetic sealing in made across the rigid extended interposer using a sterile plastic bag 213 and hermetic sealing tape 212. Across the hermetic seal, the outer region of 213 is considered sterile zone that could interface with patients and inner region of 213 is considered non-sterile zone.

Figure 2Q:
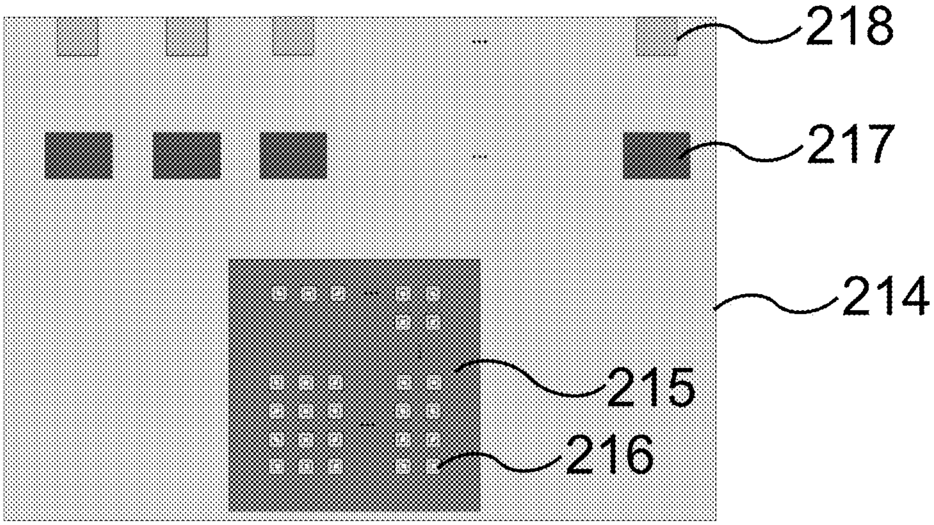
Figure 2R:
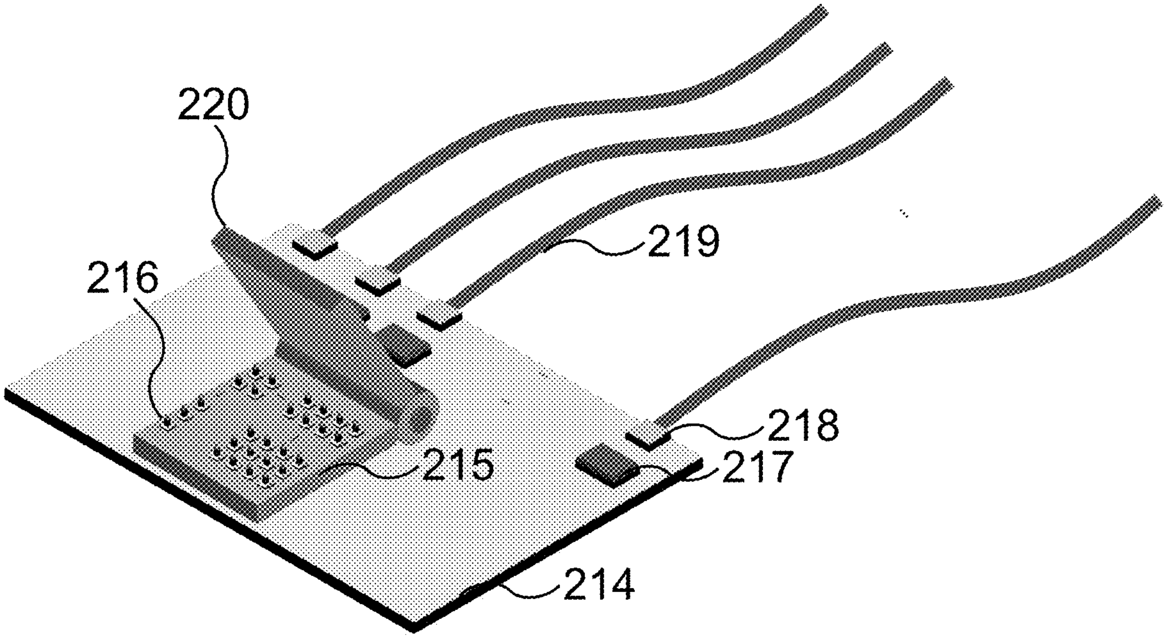

FIGS. 2Q and 2R show the acquisition board 214 populated with compact (<5 cm), high-density socket (>100 contacts/cm$^2$) 215 with high density contacts 216, amplifier chips 217, digital input/output pins 218, and digital cables 219. Many socket interconnect technologies can be adopted, ranging from more typical CPU sockets with spring-loaded pins, to more advanced conductive elastomer pad arrays.

Figure 2S:
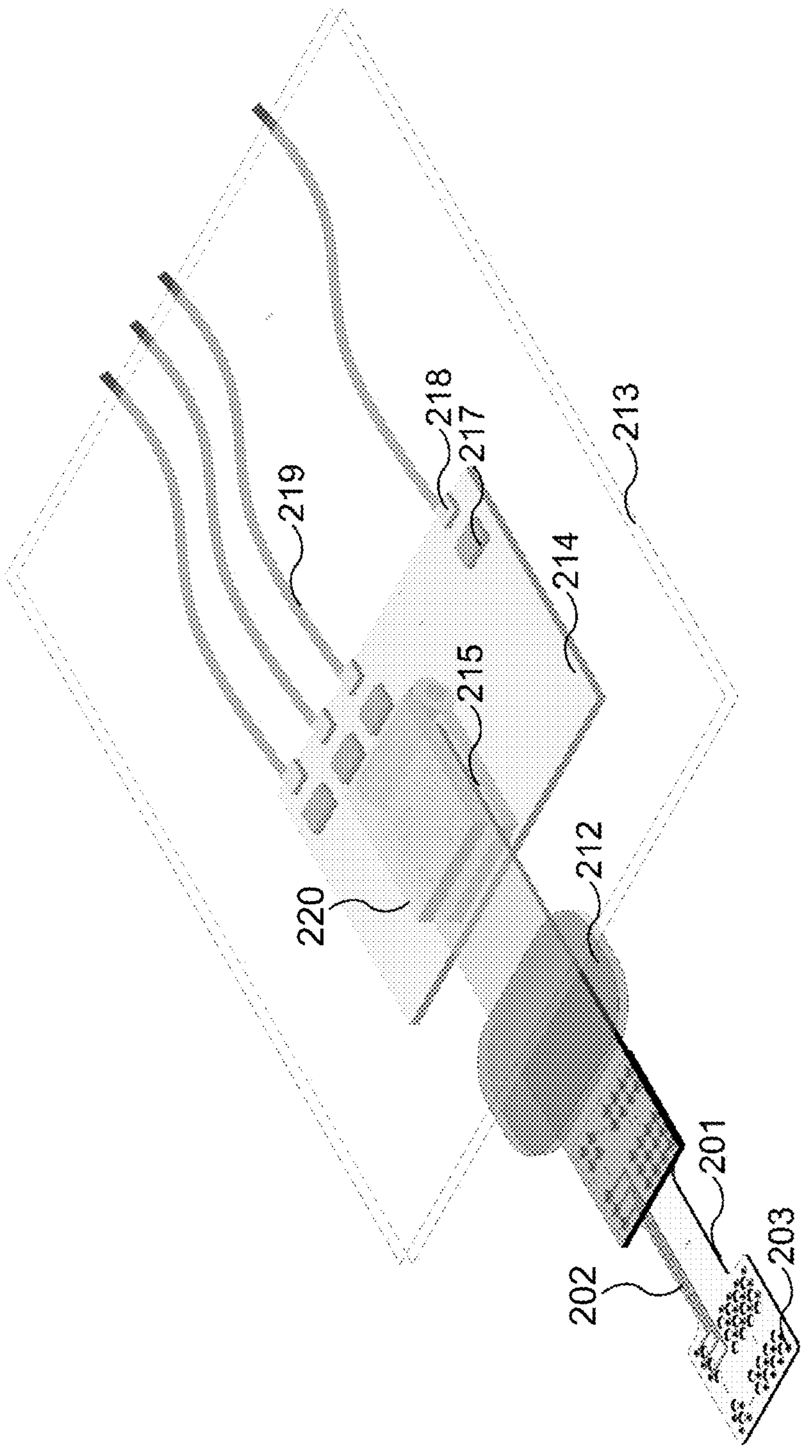

FIG. 2S illustrates how the acquisition board 214 is inserted inside the non-sterile zone of the plastic bag 213 and establishing connection with the extended interposer board with the quick (a few seconds) latching mechanism 220 which acts to press the socket contacts 216 against the interposer contact pads 210. The sockets can be compact, high-density sockets that are smaller than 5 cm and has over 100 contacts per square cm. The socket can use conductive elastomer pads, spring-loaded pins, land grid arrays, ball grid arrays, pin grid arrays, silver buttons, silver balls, or other physical means to make ohmic contact with the interposer board. The interposer board can include raised planar metallic contact pads. The interposer board can be bonded to another smaller interposer board with vias-in-pad to raise the height of the contact pads so as to properly mate with the socket. The interposer board(s) can have additional contact pads and connectors for multiple acquisition electronics to be routed to electrodes sharing the same flexible substrate so as to allow for multiple systems to record in parallel from multi-thousand or tens-of-thousand channels.

Figure 3:
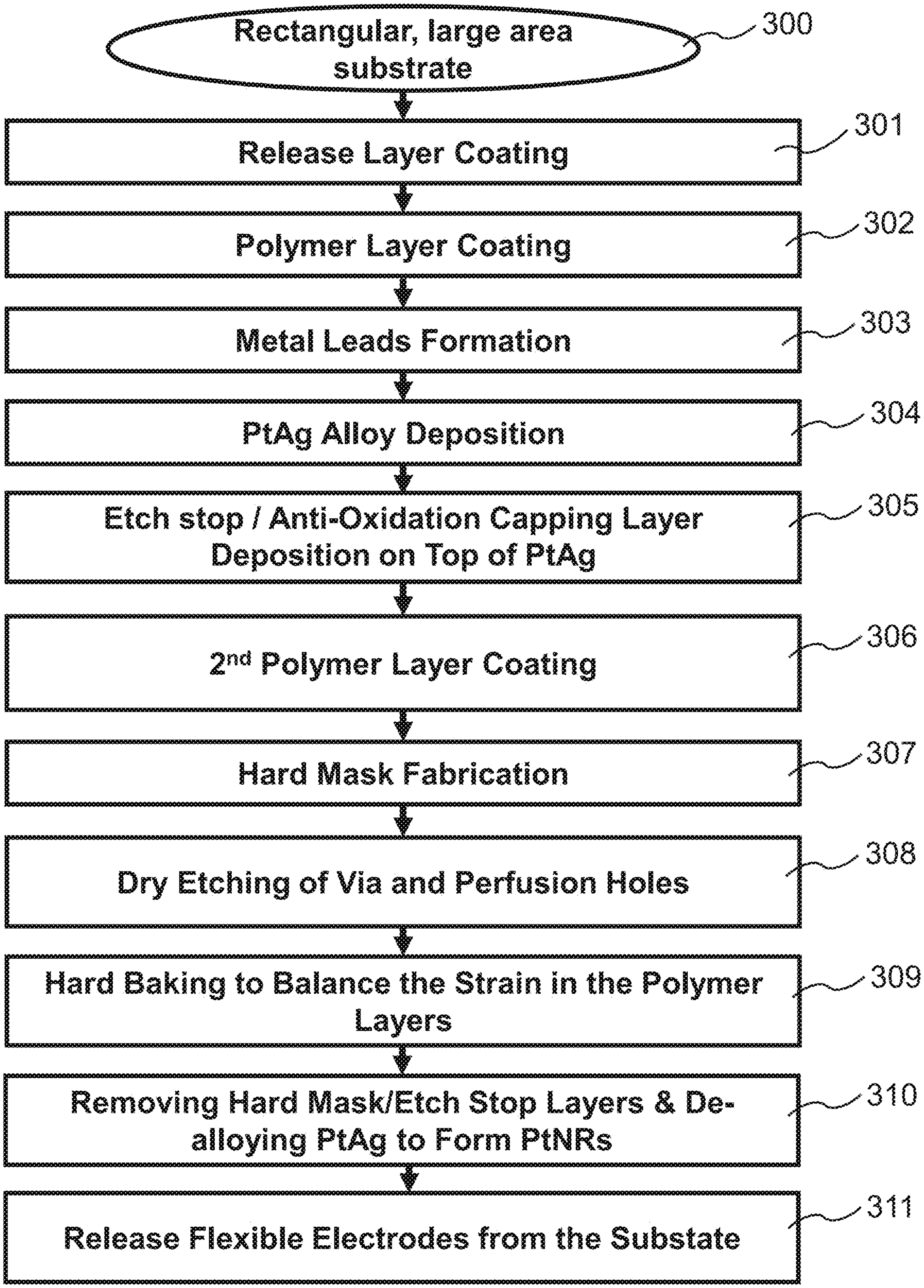
FIGS. 3A-3B are flowcharts of a preferred method for fabricating multi-thousands channel electrode array.
Figure 3B:
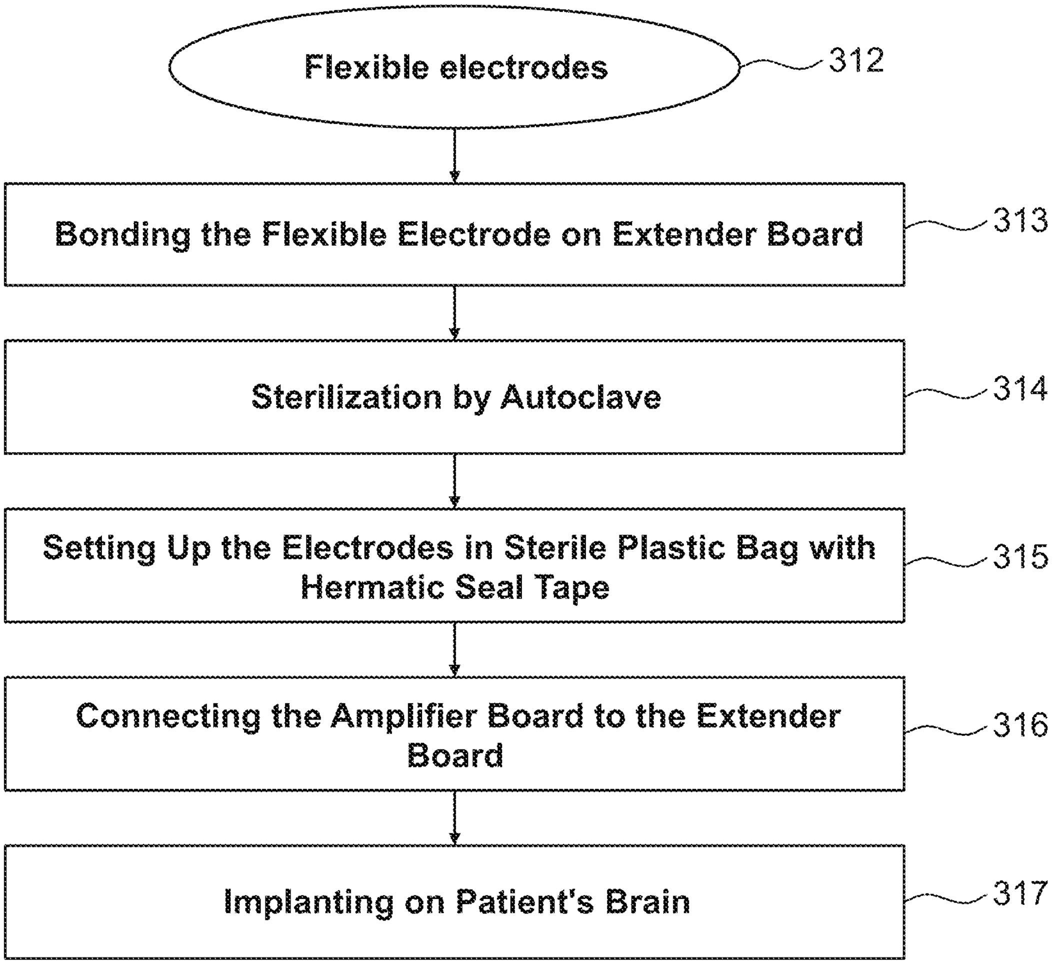
Figure 3C:
Figure 3D:
Figure 3E:
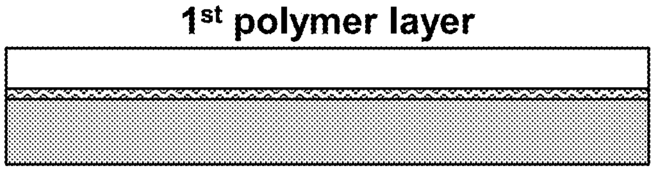
Figure 3F:
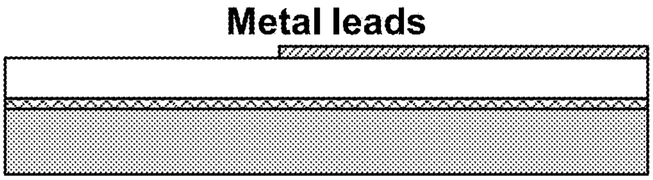
Figure 3G:
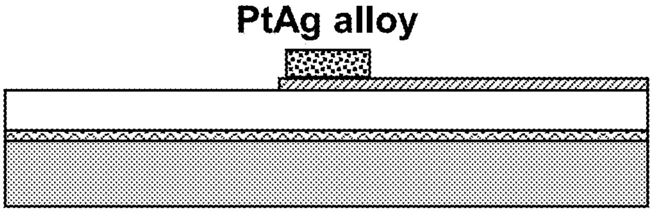
Figure 3H:
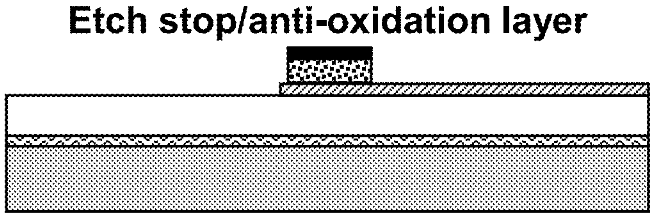
Figure 3I:
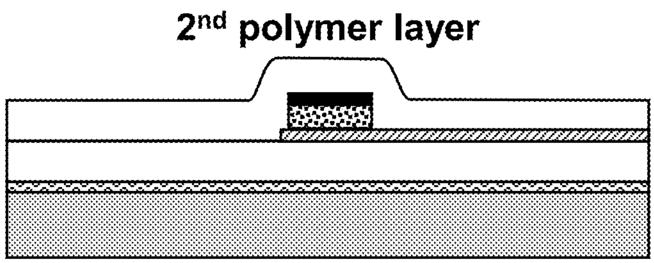
Figure 3J:
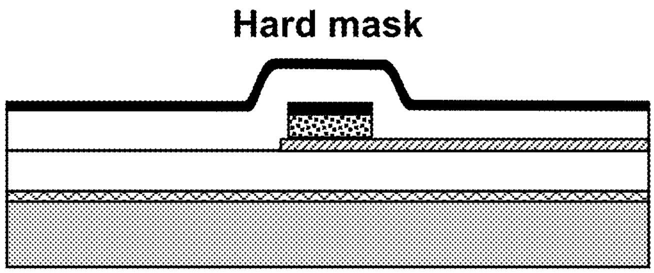
Figure 3K:
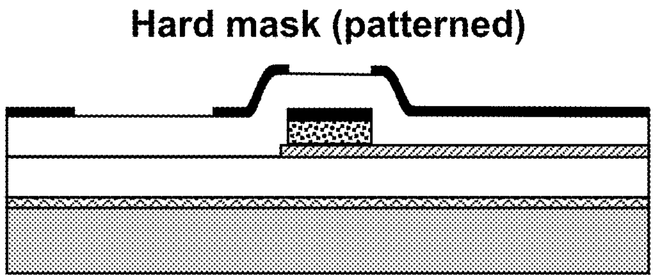
Figure 3L:
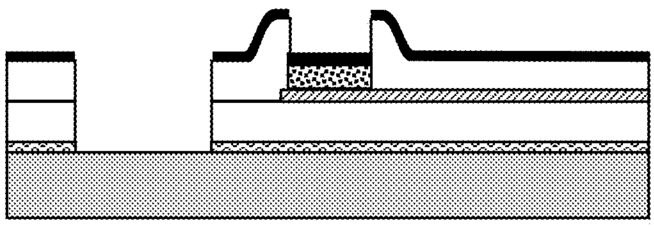
Figure 3M:
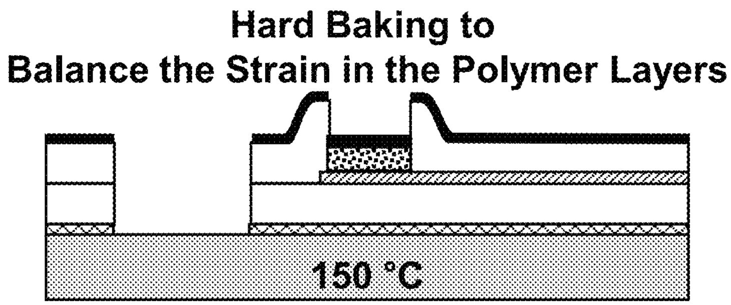
Figure 3N:
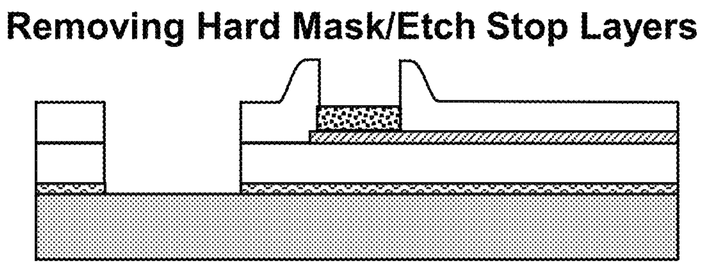
Figure 3O:
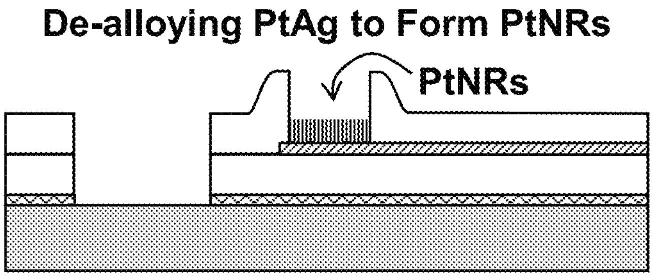
Figure 3P:
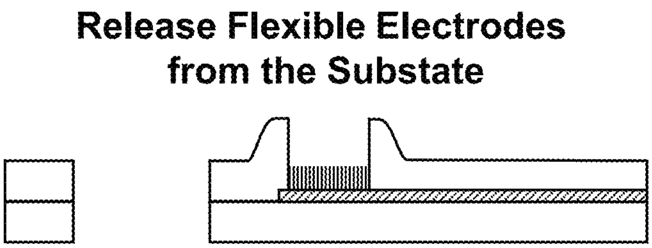

An overall preferred method is illustrated in FIGS. 3A-3P, understanding of which is also aided with reference to FIGS. 2A-2S. With reference to the steps in FIGS. 3A 3B, the corresponding cross-section view is identified in paratheses. A rigid carrier substrate is provided 300 (FIG. 3C). A release layer is deposited on the carrier substrate 301 (FIG. 3D). A thin flexible layer of non-conductive biocompatible 1$^{st}$ polymer is deposited on the release layer 302 (FIG. 3E). A pattern of elongate metal leads and electrode sites and pad sites at opposite terminal ends of the metal leads is formed 303 (FIG. 3F). Electrochemically active material, e.g. PtAg, which can be nanorods, is formed on the electrode sites 304 (FIG. 3G). Preferably, that material is coated with an etch/stop anti-oxidation capping layer 305 (FIG. 3H). This layer can be 20-100 nm, e.g. 50 nm Ti. A second non-conductive biocompatible polymer is deposited 306 to seal the leads (FIG. 3I). A mask is deposited (FIG. 3J) and then patterned with openings at the electrodes and at perfusion hole sites 307 (FIG. 3K). The perfusion holes can be 10 μm-1 cm. With 1 cm holes, there would only be a few holes, while 2 mm is a maximum preferred diameter to have perfusion holes adjacent each electrode. Perfusion holes and electrode vias are etched through the mask openings at the electrode sides to expose the electrode sites and vias through the thin flexible layer 308 (FIG. 3L). Hard baking is then conducted to balance the strain in the polymer layers 309 (FIG. 3M). For parylene C, 125-200° C. is suitable, and an example hard bake is at 150° C. for 30-90 minutes. The mask is removed (FIG. 3N) and the electrodes are de-alloyed to form platinum nanorods 310 (FIG. 3O) in a preferred embodiment. The flexible electrode array is released 311 (FIG. 3P) from the carrier substrate by dissolving the release layer.

The pad sites of the array 312 are bonded 313 to an extended board 313. The flexible electrode array and the extended board are sterilized 314, such as in an autoclave. The array and first part of the extended board are sealed 315 in a sterile plastic bag. A second part of the extended board to a circuit 316, such as an amplifier and other electronics outside the sterile plastic bag. The sterile part can be implanted 317 on a brain.

The connection method detailed above allows for the implanted electrode to be physically separated from the acquisition circuitry which is crucial for both clinical translation and commercialization. Given that the majority of the cost falls onto the acquisition circuitry, this connectorization method drastically reduces the cost of each electrode as the acquisition circuitry can be used repeatedly with different arrays that are used only for one procedure on one patient. Additionally, the implanted portion of the electrode can be easily sterilized through conventional medical autoclave processes without worrying about damaging sensitive electronics. The materials can also be easily limited to known biocompatible materials, thus safety constraints can be more easily met without the need for robust passivation of toxic or hazardous materials.

Experiments demonstrated a preferred method to fabricate thousands of channel electrode array produced high-yield (>99%) electrodes with reliable recording capability. Electrochemical properties of the electrode array were qualified in bench-top testing and we observed that they exhibit low electrochemical impedances at low frequency recordings (<30 kOhm at 1 kHz for an electrode diameter of 30 μm), important for recording boradband brain activity from local field potentials at a few Hz to single and multi-units at several kHz.

In the example experiments to demonstrate fabrication consistent with FIGS. 3A and 3B, 7"×7"×0.06" photomask grade glass substrates were used as substrate carriers for the thin parylene C layers. The mask grade soda lime glass substrates were polished and cleaned. Substrates are not limited to soda lime glass but any polished and microfabrication-grade substrate could be used. Plasma Etch PE 100 system was used for oxygen plasma treatment on the glass substrates at 200 W for 5 min. Particle filtered and diluted Micro-90 (0.1%), an anti-adhesion layer, is spun-cast at 1000 rpm on the glass substrate to facilitate the separation of the device after the device fabrication completed. A first parylene C layer (1-3 μm) is deposited by chemical vapor deposition using a PDS 2010 Parylene coater system. Metal lead patterns are defined and exposed using a Heidelberg MLA150 maskless aligner using AZ5214E-IR photoresist in an image reversal mode. Temescal BJD 1800 electron beam evaporator is used for the deposition of 10 nm Cr adhesion layer and 500 nm Au contact layer, and a lift-off process in acetone follows. Repeating the patterning and deposition of the same Cr/Au metal leads on top of the first metal leads generally increased the final device yield.

Then patterns of the electrode sites are defined using NR9-6000 negative resist and a Heidelberg MLA150 maskless aligner for exposure. A 15 nm/100 nm Cr/Pt layer is sputtered followed by deposition of ~0.5 μm thick PtAg alloy using a co-sputtering technique performed at 400 W (RF) and 50 W (DC) powers for co-deposition of Ag and Pt, respectively. A lift-off process in acetone follows shortly after.

To realize PtNR film on electrode sites, de-alloying (chemical etching) is performed (for example in Nitric acid at 60 C° for 2 min). $O_2$ plasma (Oxford Plasmalab 80 RIE) is then applied (e.g., for 1.5 min (200 W RF power)) to activate the surface of parylene C for enhancing the adhesion of the subsequent encapsulating parylene C layer. A layer of—1-3 μm parylene C is then deposited and followed by coating of 50-nm-thick Ti hard mask. Then AZ5214E-IR photoresist is spun-cast and patterned, which is exposed and developed with MIF 300 developer. Ar and $SF_6$ plasma are used to etch the openings in the Ti hard mask and the parylene C layers. After completing the dry etching steps, the substrate was cured at 150° C. for 40 min to balance the internal strain in parylene C layers. Finally, the electrodes are immersed in 1:6 buffered oxide etchant for to remove the Ti hard mask, and the device is then immersed in 60° C. nitric acid for 2 min to complete de-alloying of PtAg alloy to form Pt nanorods. The released flexible electrode array then interfaced to the extended interposer using conducting epoxy boning.

Figure 4A:
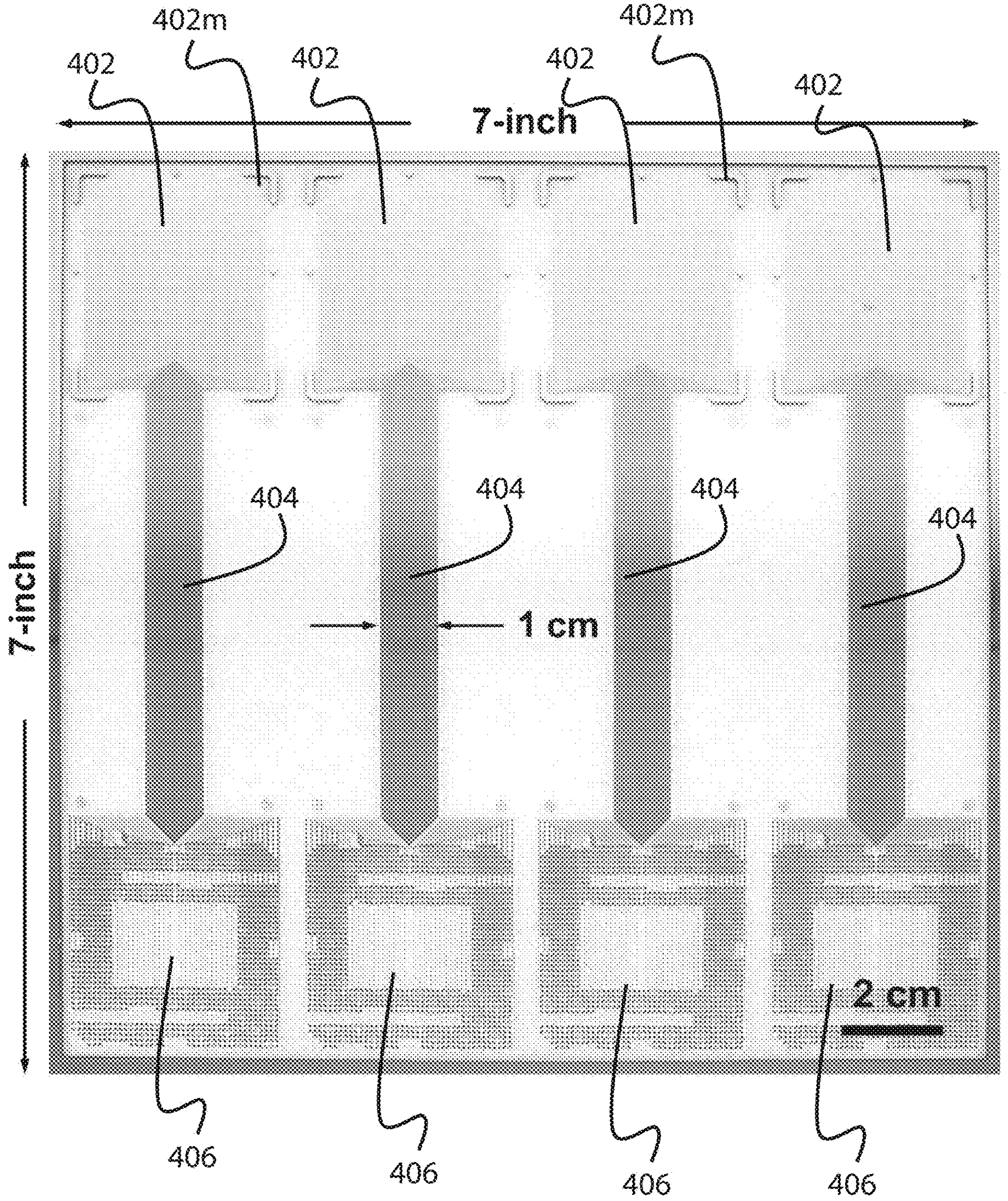
FIGS. 4A-4F are images of a prototype multi-thousand channel electrode array at different magnifications, amplification board with a high-density socket, and a set-up of the array in an operation room.

FIG. 4A shows a picture of a carrier substrate with four fabricated multi-thousand channel electrophysiology PtNR device on thin film parylene C layer coated on 7"×7" photomask grade soda lime glass substrate, showing 4 microarrays 402, each having 1024 microdots as electrode sites at the top of each of the four cortical probes and a set of imaging markers 402*m* around the microarrays 402. Each microdot electrode site is connected to its own metal lead in an array of long and narrow metal leads 404. Contact pad arrays 406 include individual connections to the leads 404 and a corresponding electrode in the microarrays 403. Individual contact pads in the arrays 406 can bond with corresponding connections of an interposer. In the example of FIG. 4A, each cortical array device includes an approximate 4 cm×4 cm microarray 402 and a 4 cm×4 cm contact pad array 406. The lead arrays 404 were approximately 1 cm wide and 7 cm long.

Figure 4B:
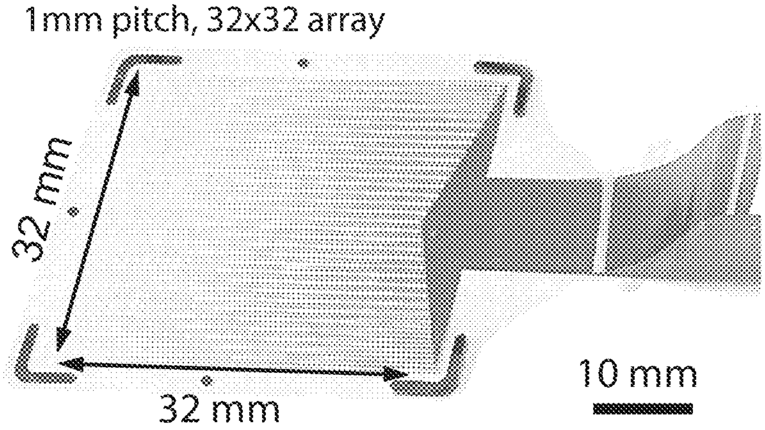
Figure 4C:
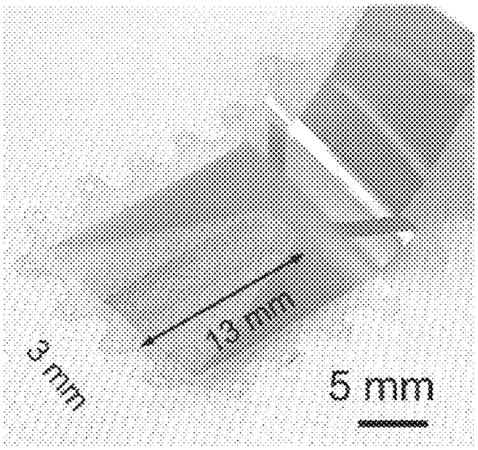
Figure 4D:
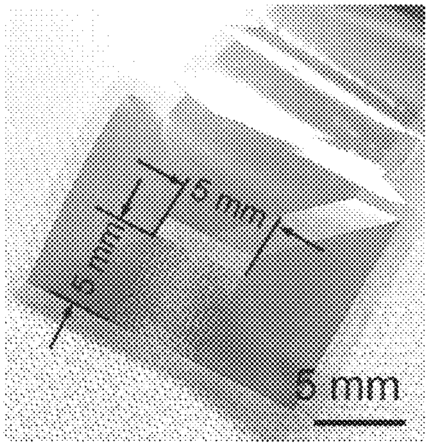

FIGS. 4B-4D shows pictures of a 1024-ch electrode arrays 402 with different sizes and densities. In FIG. 4B, the array is 32 mm×32 mm with electrode sites at a 1 mm pitch. In FIG. 4C, the array is 13 mm×3 mm with electrode sites in a truncated pyramid shape at a 200 μm pitch. In FIG. 4D, the array extends 5 mm×5 mm with electrode sites at a 150 μm mm pitch.

Figure 4E:
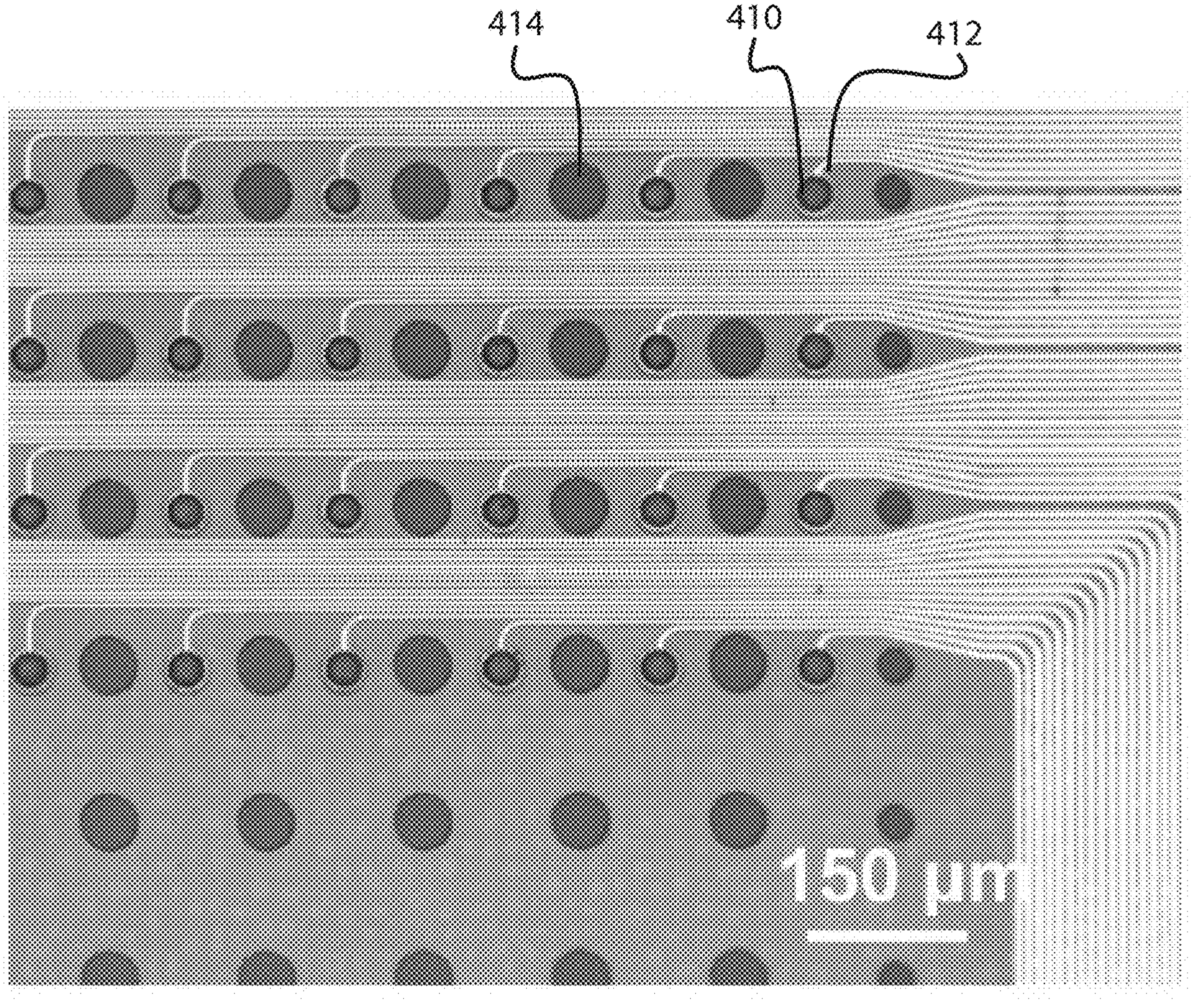
Figure 4F:
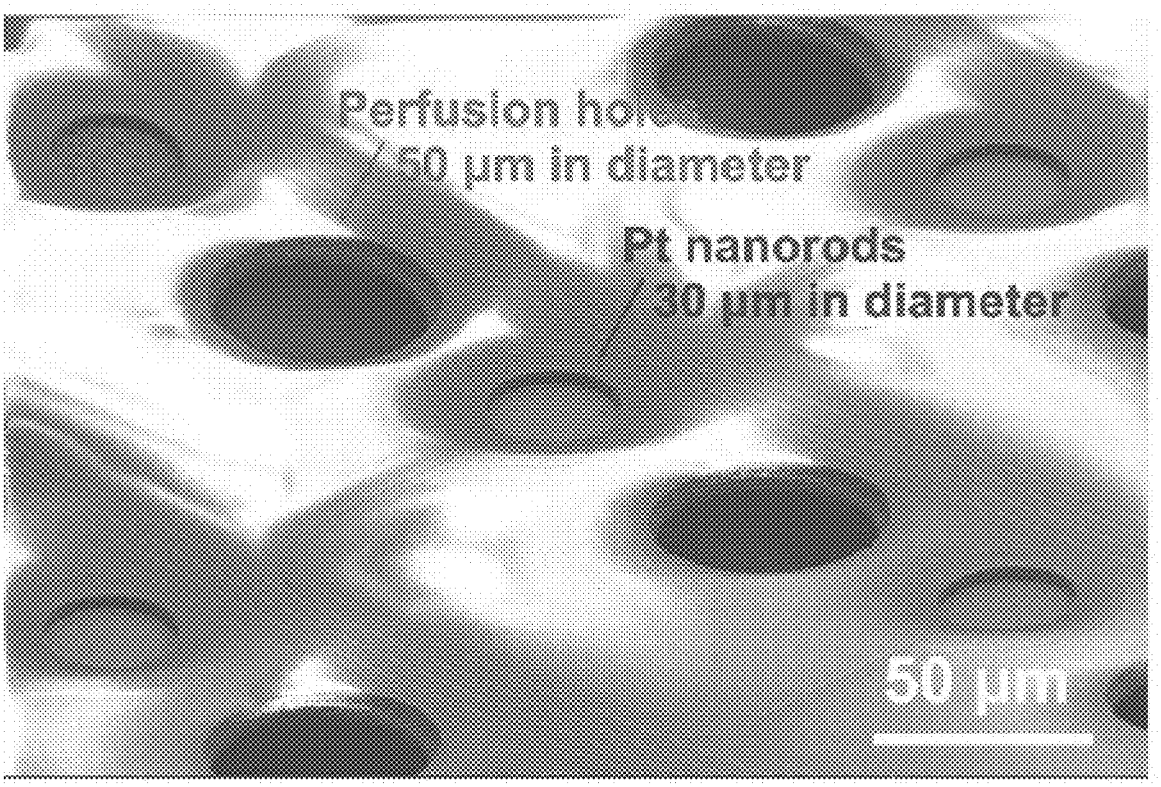

FIG. 4E, a local magnified view of a portion of a multi-thousand channels Pt nanorods micro-electrode (Diameter=30 μm) array and its electrode lead pattern is shown. A number of Pt nanorods micro-electrode 410 are shown with connections to individual leads 412. Through perfusion holes 414 are formed between the nanorod recording sites to perfuse excess cortical fluid that will ensure that the recording sites remain close enough to the tissues of interest. Electrochemical impedance magnitude histogram show that the electrode has very uniform impedance magnitude (average 11 kOhm at 1 kHz with standard deviation of 2 kOhm), and the electrode array have a high yield (99.4%). FIG. 4F shows an example array that includes Pt nanorods that were 30 μm in diameter and perfusion through-holes that were 50 μm in diameter.

Figure 4G:
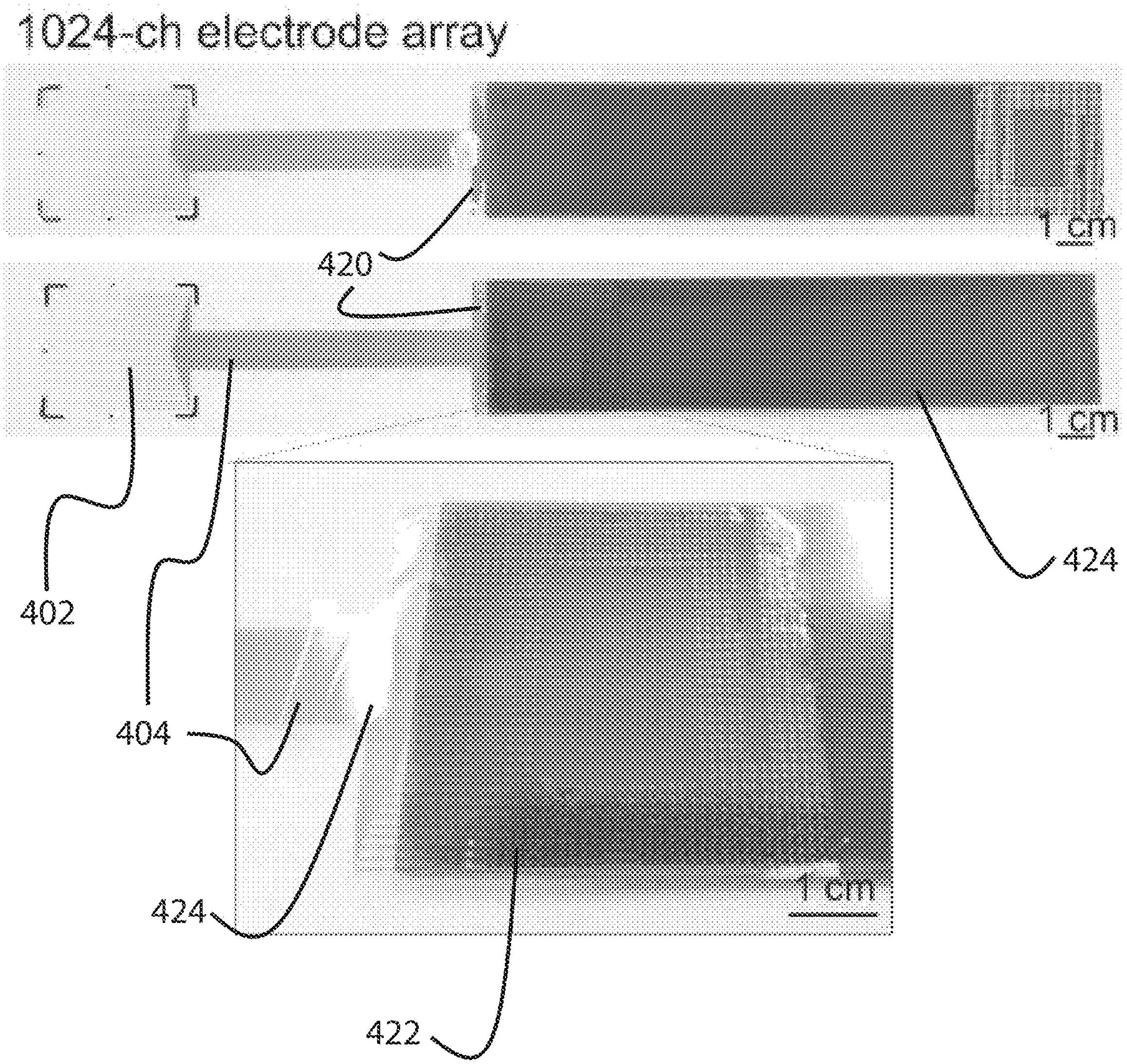
Figure 4H:
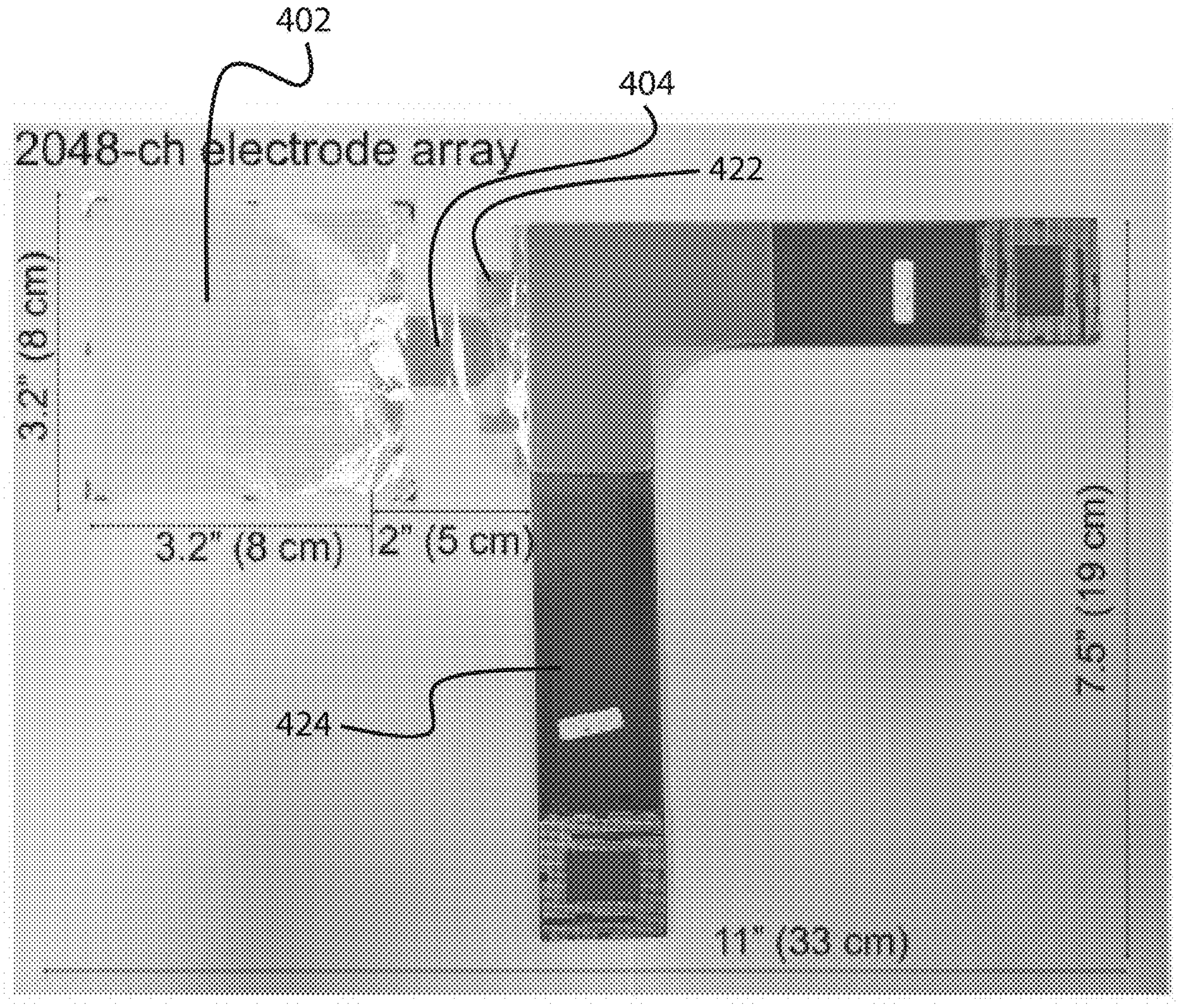

FIGS. 4G and 4H are photos of the multi-thousand channel electrode bonded on a rigid extended interposer 420 by the conductive epoxy bonding method to a contact pad 422. Upper panel shows the front and the backsides of 1024-channel electrodes, and the bonding interfacial region is magnified. Lower panel shows 2048-channels electrode arrays boned with joined extender interposer boards. The interposers are joined by autoclave-compatible adhesive and a laser cut FR4 board 424. A plastic envelope 426 seals the sterile array portions including the contact pad portion 422 of the interposer 420.

The multi-thousand channel cortical electrode arrays enable 100 times higher spatial resolution over broader areas. The invention supports greater spatial localization of neurophysiological activity, thereby improving resection boundaries in advanced neurosurgeries. The multi-thousand channel cortical electrode arrays can be composed only of passive elements, so, unlike implantable devices integrated with active electronics units, the electrodes are compatible with conventional medical grade sterilizers. A CPU style connector allowed instantaneous and reliable connection between thousands of passive electrodes to an acquisition board in the operating room. Additionally, the multi-thousand channel cortical electrode arrays have micro-hole arrays throughout the gird which allowed the clinical Ojemann clinical stimulation electrode to directly stimulate the cortical surface through the grid.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A flexible electrode array with hundreds or thousands channels for clinical use comprising:

an array of at least hundreds of electrodes on a flexible biocompatible polymer substrate;

a plurality of perfusion through-holes through the substrate;

individual elongate lead connections to each of the electrodes, the elongate lead connections being supported by the flexible biocompatible polymer substrate and extending away from the array;

flexible biocompatible polymer insulating the individual elongate lead connections and supporting the array;

an interposer with individual channel connections conductively bonded to the individual elongate lead connections; and packaging enclosing a portion of the interposer, where the outer side of the packaging including the array and individual elongate lead connections is sterile while a portion of interposer within the packaging is non-sterile.

2. The flexible electrode array of claim 1, wherein the electrodes comprise nanorod electrodes.

3. The flexible electrode array of claim 1, wherein total thickness of the array is 2-20 μm.

4. The flexible electrode array of claim 1, wherein the electrodes comprise platinum (Pt nanorods and/or PEDOT: PSS.

5. The flexible electrode array of claim 1, wherein the flexible biocompatible polymer comprises parylene C.

6. The flexible electrode array of claim 1, wherein the diameters of perfusion through holes are in the range of 10 μm-1 cm.

7. The flexible electrode array of claim 1, wherein the plurality of perfusion through-holes comprises a perfusion through-hole adjacent each of the electrodes.

8. The flexible electrode array of claim 1, wherein the portion of the interposer inside the packaging is configured to connect to a circuit board within the packaging.

9. The flexible electrode array of claim 8, wherein the interposer is connected to the circuit board within the packaging, and wherein the circuit board comprises a data acquisition board.

10. The flexible electrode array of claim 9, comprising a socket and a latch that connect the interposer with the data acquisition board.

11. The flexible electrode array of claim 1, wherein the array comprises a planar array and the packaging forms a hermetic seal across the individual channel connections of the rigid extended interposer.

12. The flexible electrode array of claim 1, wherein the portion of interposer within the packaging includes a portion individual channel connections.

13. The flexible electrode array of claim 1, wherein the packaging comprises a sterile plastic bag and the seal comprises sterile hermetic sealing tape.

* * * * *